US00RE42934E

(19) United States
(12) Reissued Patent
Thompson

(10) Patent Number: US RE42,934 E
(45) Date of Reissued Patent: Nov. 15, 2011

(54) WORLD WIDE PATIENT LOCATION AND DATA TELEMETRY SYSTEM FOR IMPLANTABLE MEDICAL DEVICES

(75) Inventor: David L. Thompson, Andover, MN (US)

(73) Assignee: Medtronic, Inc., Minneapolis, MN (US)

(21) Appl. No.: 11/541,521

(22) Filed: Sep. 29, 2006

Related U.S. Patent Documents

Reissue of:
(64) Patent No.: 6,083,248
Issued: Jul. 4, 2000
Appl. No.: 09/198,623
Filed: Nov. 24, 1998

U.S. Applications:
(63) Continuation-in-part of application No. 09/045,275, filed on Mar. 20, 1998, now Pat. No. 6,292,698, which is a continuation of application No. 08/494,218, filed on Jun. 23, 1995, now Pat. No. 5,752,976.

(51) Int. Cl.
*A61N 1/36* (2006.01)
(52) U.S. Cl. ..... 607/30; 607/32; 607/60
(58) Field of Classification Search ..... 607/9–32, 607/59, 60; 128/903, 904
See application file for complete search history.

(56) References Cited

U.S. PATENT DOCUMENTS 3,253,588 A 5/1966 Vuilleumier et al.
3,518,997 A 7/1970 Sessions
(Continued)

FOREIGN PATENT DOCUMENTS

DE 44 01 443 A1 8/1994
(Continued)

*Primary Examiner* — Scott M Getzow
(74) *Attorney, Agent, or Firm* — Shumaker & Sieffert, P.A.

(57) ABSTRACT

A system for communicating with a medical device implanted in an ambulatory patient and for locating the patient in order to selectively monitor device function, alter device operating parameters and modes and provide emergency assistance to and communications with a patient. The implanted device includes a telemetry transceiver for communicating data and operating instructions between the implanted device and an external patient communications control device that is either worn by or located in proximity to the patient within the implanted device tranceiving range. The control device preferably includes a communication link with a remote medical support network, a global positioning satellite receiver for receiving positioning data identifying the global position of the control device, and a patient activated link for permitting patient initiated personal communication with the medical support network. A system controller in the control device controls data and voice communications for selectively transmitting patient initiated personal communications and global positioning data to the medical support network, for initiating telemetry out of data and operating commands from the implanted device and transmission of the same to the medical support network, and for receiving and initiating re-programming of the implanted device operating modes and parameters in response to instructions received from the medical support network. The communications link between the medical support network and the patient communications control device may comprise a world wide satellite network, hard-wired telephone network, a cellular telephone network or other personal communications system. Methods and apparatae are also described that enhance the ability of the medical system to find patients and to get reports on patient and medical device status, and even update medical device programming using such facilities, and others described in detail within.

69 Claims, 9 Drawing Sheets

U.S. PATENT DOCUMENTS 3,623,486 A 11/1971 Berkovitz et al.
3,631,860 A 1/1972 Lopin
3,738,369 A 6/1973 Adams et al.
3,768,014 A 10/1973 Smith et al.
3,769,965 A 11/1973 Raddi et al.
3,805,796 A 4/1974 Terry, Jr. et al.
3,885,552 A 5/1975 Kennedy
3,910,257 A 10/1975 Fletcher et al.
3,973,320 A 8/1976 Greco et al.
4,066,086 A 1/1978 Alferness et al.
4,208,008 A 6/1980 Smith
4,211,235 A 7/1980 Keller, Jr. et al.
4,223,679 A 9/1980 Schulman et al.
4,233,985 A 11/1980 Hartlaub et al.
4,236,524 A 12/1980 Powell et al.
4,250,884 A 2/1981 Hartlaub et al.
4,253,466 A 3/1981 Hartlaub et al.
4,273,132 A 6/1981 Hartlaub et al.
4,273,133 A 6/1981 Hartlaub et al.
4,319,241 A 3/1982 Mount
4,374,382 A 2/1983 Markowitz
4,401,120 A 8/1983 Hartlaub et al.
4,440,173 A 4/1984 Hudziak et al.
4,531,523 A 7/1985 Anderson
4,539,992 A 9/1985 Calfee et al.
4,550,732 A 11/1985 Batty, Jr. et al.
4,571,589 A 2/1986 Slocum et al.
4,601,291 A 7/1986 Boute et al.
4,675,656 A 6/1987 Narcisse
4,676,248 A 6/1987 Bernsteon
4,827,943 A 5/1989 Bornn et al.
4,889,131 A 12/1989 Salem et al.
4,981,141 A 1/1991 Segalowitz
4,987,897 A * 1/1991 Funke ..... 607/32
5,036,869 A 8/1991 Inahara
5,113,859 A 5/1992 Funke
5,113,869 A 5/1992 Nappholz et al.
5,127,404 A 7/1992 Wyborny et al.
5,321,618 A 6/1994 Gessman
5,336,245 A 8/1994 Adams et al.
5,381,798 A 1/1995 Burrows
5,416,695 A * 5/1995 Stutman et al. ..... 600/300
5,433,736 A 7/1995 Nilsson
5,490,073 A * 2/1996 Kyrtsos ..... 701/207
5,544,661 A * 8/1996 Davis et al. ..... 600/513
5,583,517 A 12/1996 Yokev et al.
5,592,173 A 1/1997 Lau et al.
5,593,426 A 1/1997 Morgan et al.
5,626,630 A 5/1997 Markowitz et al.
5,680,140 A 10/1997 Loomis
5,689,431 A 11/1997 Rudow et al.
5,720,770 A 2/1998 Nappholz et al.
5,731,768 A 3/1998 Tsang
5,745,868 A 4/1998 Geier
5,777,580 A 7/1998 Janky et al.
5,784,339 A 7/1998 Woodsum et al.
5,874,897 A 2/1999 Klempau et al.

FOREIGN PATENT DOCUMENTS

FR 72.05963 2/1972
FR 72.05963 2/1978
FR 2 624 749 A1 6/1989

* cited by examiner

WORLD WIDE PATIENT LOCATION AND DATA TELEMETRY SYSTEM FOR IMPLANTABLE MEDICAL DEVICES

Matter enclosed in heavy brackets [ ] appears in the original patent but forms no part of this reissue specification; matter printed in italics indicates the additions made by reissue.

This application is a [CIP] *continuation-in-part of* 09/045,275, filed Mar. 20, 1998, now [abandoned] *U.S. Pat. No. 6,292,698*, [and] *which is* a [CON] *continuation* of 08/494,218, filed Jun. 23, 1995, now U.S. Pat. No. 5,752,976.

FIELD OF THE INVENTION

The present invention relates to communication systems for communicating with an implanted medical device or device system, and more particularly, such a communication system that may function on a world wide basis at any time to communicate patient location, device monitoring data, device re-programming data and to allow for effective response to emergency conditions.

The following references were cited in commonly assigned, U.S. Pat. No. 5,683,432 for ADAPTIVE, PERFORMANCE-OPTIMIZING COMMUNICATION SYSTEM FOR COMMUNICATING WITH AN IMPLANTABLE DEVICE by S. Goedeke et al. to indicate the prior state of the art in such matters. In particular, in reed switch use U.S. Pat. No. 3,311,111 to Bowers, U.S. Pat. No, 3,518,997 to Sessions, U.S. Pat. No. 3,623,486 to Berkovits, U.S. Pat. No, 3,631,860 to Lopin, U.S. Pat. No. , 3,738,369 to Adams et al., U.S. Pat. No. 3,805,796 to Terry, Jr., U.S. Pat. No. 4,066,086 to Alferness et al.; informational type U.S. Pat. No. 4,374,382 to Markowitz, U.S. Pat. No, 4,601,291 to Boute et al.; and system U.S. Pat. No. 4,539,992 to Calfee et al., U.S. Pat. No. 4,550,732 to Batty Jr., et al., U.S. Pat. No, 4,571,589 to Slocum et al., U.S. Pat. No. 4,676,248 to Berntson, U.S. Pat. No. 5,127,404 to Wyborny et al., U.S. Pat. No. No. 4,211,235 to Keller, Jr. et al., U.S. patents to Hartlaub et al., U.S. Pat. No. 4,250,884, U.S. Pat. No. 4,273,132, U.S. Pat. No. 4,273,133, U.S. Pat. No. 4,233,985, U.S. Pat. No. 4,253,466, U.S. Pat. No. 4,401,120, U.S. Pat. No. 4,208,008, U.S. Pat. No. 4,236,524, U.S. Pat. No. 4,223,679 to Schulman et al., U.S. Pat. No. 4,542,532 to McQuilkin, and U.S. Pat. No. 4,531,523 to Anderson.

BACKGROUND OF THE INVENTION

Over the years, many implantable devices have been developed to monitor medical conditions and deliver therapy to a patient. Such devices included electrical stimulation devices for stimulating body organs and tissue to evoke a response for enhancing a body function or to control pain, and drug delivery devices for releasing a drug bolus at a selected site. Other more passive implantable and wearable medical devices have been developed for monitoring a patient's condition.

We will refer to devices that are implantable as IMD's or simply MD's to indicate that they may be implantable or wearable. We will occasionally also refer to the device having GPS and transmitter for keeping in touch with the medical network or satellites as a belt worn device or simply a belt device, although it is understood that the requirement for the device is proximity to the patient with the medical device, (the IMD or MD), meaning it can be worn as a pendent, on the neck, wrist, ankle, or the like.

Chronically implanted cardiovascular devices for monitoring cardiovascular conditions and providing therapies for treating cardiac arrhythmias have vastly improved patients quality of life as well as reduced mortality in patients susceptible to sudden death due to intractable, life threatening tachyarrhythmias. As implanted device technology has grown more sophisticated with capabilities to discover, monitor and affect more patient conditions (including otherwise life threatening conditions) patients have enjoyed freedom from hospital or home confinement or bed rest. However, the improved mobility brings with it the need to maintain communications with the patient and the implanted device.

Early in the development of cardiac pacemakers, patient follow-up to monitor pacemaker operation was facilitated by telephonic transmissions of skin surface ECGs in real time to a physician's office employing such systems as the MEDTRONIC® TeleTrace® ECG transmitter. Over time, various patient worn, ambulatory ECG and device monitors have been developed for providing ECG data for remote analysis of cardiac arrhythmias. Also, the remotely programmable modes of operation of implantable medical devices increased, and programming methods improved.

In current arrhythmia control devices, (e.g. cardiac pacemakers, and pacemaker-cardioverter-defibrillators) a relatively wide range of device operating modes and parameters are remotely programmable to condition the device to diagnose one or more cardiac arrhythmia and deliver an appropriate therapy. In cardiac pacemakers, the pacing rate in one or both heart chambers is governed by algorithms that process the underlying cardiac rhythm as well as physiologic conditions, e.g. patient activity level and other measured variables, to arrive at a suitable pacing rate. The pacemaker operating modes and the algorithm for calculation of the appropriate pacing rate are programmed or reprogrammed into internal memory by accessing the implanted pacemaker's telemetry transceiver with an external programmer. Even the diagnosis of a tachyrhythmia requiring delivery of a treatment therapy and the therapies to be delivered may now be governed by operating modes and algorithm parameters that can be programmed into and changed using such a programmer.

Such implanted devices can also process the patient's electrogram and any measured physiological conditions employed in the diagnosis and store the data, for subsequent telemetry out on interrogation by the external programmer. The telemetered out data is analyzed and may be employed to establish or refine the operating modes and parameters by a doctor to adjust the therapies the device can deliver. In general, the manner of communicating between the transceivers of the external programmer and the implanted device during programming and interrogating is referred to as telemetry.

Initially, when programming techniques were first devised, the paramount concern addressed related to patient safety. Safeguards addressed the concern that the patient could be put at risk of inadvertent mis-programming of the implanted device, e.g. by stray electromagnetic fields. For this reason, and in order to avoid high current consumption that would shorten the implanted device battery life, telemetry operating range was extremely limited. In systems continuing to the present time, telemetry has required application of a magnetic field at the patient's skin over the implanted device to close a reed switch while RF programming or interrogating commands are generated to be received by the implanted device transceiver. The programming or interrogating commands are decoded and stored in memory or used to trigger telemetry out of stored data and operating modes and parameters by the implanted device transceiver.

As stated at the outset, one of the rationales and attributes of implanted medical devices of the type described, is that the patient is allowed to be ambulatory while his medical condition is monitored and/or treated by the implanted medical device. As a further safety precaution, "programmers" (devices capable of programming all the operating modes or functions of the implanted device and for initiating interrogation through the telemetry system) are generally not provided to the patients. Patients are periodically examined and device interrogation is conducted by the physician using the external "programmer" during follow-up visits to the physicians office or clinic. This limits the frequency of monitoring and may require certain patients to remain close to the physician's office, and/or limit their life style options (i.e., remain in or near their home).

Emergency conditions (device failure, physiologic variable changes resulting in inappropriate therapy, transient conditions/problems) may require additional monitoring or follow-up.

The short range of conventional device telemetry is itself viewed as unduly limiting of a patient's mobility. In the medical monitoring field, longer range, continuously accessible telemetry has been sought and systems for doing so have been proposed. In U.S. Pat. No. 5,113,869 for example, an implanted ambulatory ECG patient monitor is described that is provided with longer range telemetry communication with a variety of external accessory devices to telemeter out alarm signals and ECG data and to receive programming signals. The high frequency RF signals are encoded, including the implanted device serial number, to ensure that the communication is realized only with the proper implanted device and that it is not mis-programmed.

Telemetry communication with other implanted devices, particularly drug infusion pumps or pacemaker-cardioverter-defibrillator devices, to initiate or control their operation is also disclosed. Communication between the implanted AECG monitor and an external defibrillator is also suggested through low current pulses transmitted from the defibrillator paddles through the body link in order to condition the implanted AECG monitor to provide telemetry signals to the external defibrillator.

One of the external devices disclosed in the 869 patent is a wrist worn, personal communicator alarm for responding to a telemetered out signal and emitting a warning to the patient when the implanted AECG monitor has detected an arrhythmia. The patient is thereby advised to take medications or contact the physician or to initiate external cardioversion. The personal communicator alarm also includes a transceiver and may also be used to control certain functions of the implanted AECG monitor. A further, belt worn "full disclosure recorder" is disclosed with high capacity memory for receiving and storing data telemetered out of the implanted AECG monitor when its memory capacity is exhausted.

A remote, external programmer and analyzer as well as a remote telephonic communicator are also described that may be used in addition to or alternately to the personal communicator alarm and/or the full disclosure recorder. The programmer and analyzer may operate at a distance to the implanted AECG monitor to perform programming and interrogation functions. Apparently, the implanted AECG may automatically transmit a beacon signal to the programmer and analyzer to initiate an interrogation function to transmit data to the programmer and analyzer on detection of an arrhythmia or a malfunction of the implanted AECG monitor detected in a self-diagnostic test. Or by setting a timer in the personal communicator alarm, the implanted AECG monitor may be automatically interrogated at preset times of day to telemeter out accumulated data to the telephonic communicator or the full disclosure recorder. The remote telephonic communicator may be part of the external programmer and analyzer and is automatically triggered by the alarm or data transmission from the implanted AECG monitor to establish a telephonic communication link and transmit the accumulated data or alarm and associated data to a previously designated clinic or physician's office through a modem.

The combination of external devices provided to a given patient is at the discretion of the physician. It is preferred that at least the patient be provided with the external programmer and analyzer including a communications link.

A similar programmer/interrogator for an implanted pacemaker-cardioverter-defibrillator device is disclosed in U.S. Pat. No. 5,336,245, wherein the data accumulated in the limited capacity memory implanted device is telemetered out to a larger capacity, external data recorder. The accumulated data is also forwarded to a clinic employing an auto-dialer and FAX modem resident in a personal computer-based, programmer/interrogator.

In each of these disclosed systems, presumably, the patient is able to communicate with the physician's office or clinic contemporaneously with the transmission of data by modem. In all such telemetry systems for programming an operating mode or parameter or interrogating accumulated patient data or device operating modes and parameters, the patient is located within a short range, typically within sight, of the remote devices, particularly the remote programmer. If the patient is out of range of the programmer and an attached telephone system, the security of the patient is diminished. Consequently, at risk patients are advised to remain close by to the programmer and telephone for their safety.

The performance over time of implanted medical devices in the implant population is informally monitored by the periodic patient follow-ups employing the telemetry system conducted by the physician and the reporting of device malfunctions from the physician to the device manufacturer. Moreover, operating algorithm improvements developed over time to counter adverse device performance reports or to simply improve device function are provided to physicians to employ in re-programming the implanted devices at the next patient follow-up.

Although significant advances have been made in allowing patient's who are dependent on implanted medical devices to be ambulatory and still allow for monitoring of the device operation or the patient's underlying condition, a need remains to expand patient security while allowing the ambulatory patient to range widely. Telemetry systems in current use require prepositioning of the telemetry head over the implanted medical device, although the telemetry systems described above may offer the possibility of telemetry at a distance of several meters. In any case, such telemetry systems cannot communicate patient device information (uplink telemetry) or accept re-programming (downlink telemetry) when the patient is in remote or unknown locations vis-a-vis the physician of medical support network. In certain patient conditions, the inability to communicate with the medical implant can significantly increase patient mortality or cause serious irreversible physical damage.

SUMMARY OF THE INVENTION

It is therefore an object of the present invention to provide a patient data communication system for world wide patient location and data and re-programming telemetry with a medical device implanted in the patient.

It is a further object of the present invention to address the above described problems by providing such a communication system allowing the device and/or patient to communicate with support personnel at any time and from any place.

It is a still further object of the invention to allow the medical device and patient to be accurately and automatically located enabling prompt medical assistance if necessary.

These and other objects of the invention are realized in a first aspect of the invention in a system for communicating patient device information to and from a medical device implanted in an ambulatory patient and with a remote medical support network comprising: an implanted device telemetry transceiver within the implanted medical device for communicating data and operating instructions to and from the medical device in a coded communication, the implanted device telemetry transceiver having a transceiving range extending outside the patient's body a predetermined distance sufficient to receive and transmit coded telemetry communications at a distance from the patient's body; and an external patient communications control device adapted to be located in relation to the patient within the device transceiving range having a system controller for facilitating communications, an implant wireless interface including a control device telemetry transceiver for receiving and transmitting coded communications between the system controller and the implant device telemetry transceiver, a global positioning system coupled to said system controller for providing positioning data identifying the global position of the patient to the system controller; communications means for communicating with the remote medical support network; and communications network interface means coupled to the system controller and the communications means for selectively enabling the communications means for transmitting the positioning data to the medical support network and for selectively receiving commands from the medical support network.

Preferably the system further comprises an external patient communications device adapted to be located in relation to the patient within the device transceiving range for providing patient voice and data communications with the system controller, so that patient voice communications may be effected through the communications interface means and the communications means with the remote medical support network.

Furthermore, the communications interface means may effect two-way communication of voice and/or data between the remote medical support network and the patient communications device and implanted device telemetry transceiver by inclusion of cards for accessing one or all of the communications means including a cellular telephone network and a satellite-based telecommunication network, a hard-wired telephone communications system and/or a hard-wired interface for computer based system for local area and for modem-based e-mail communications systems. The cards are preferably interchangeable to fit the application needed by the particular patient.

The communications interface means preferably include two-way voice communications between the patient and the medical support network and two-way data communications for selectively receiving interrogation or programming commands from the medical support network to interrogate or program the operation of the device operation and to interrogate patient location.

The present invention allows the residential, hospital or ambulatory monitoring of at-risk patients and their implanted medical devices at any time and anywhere in the world. The medical support staff at a remote medical support center may initiate and read telemetry from the implanted medical device and reprogram its operation while the patient is at very remote or even unknown locations anywhere. Two-way voice communications with the patient and data/programming communications with the implanted medical device may be initiated by the patient or the medical support staff. The location of the patient and the implanted medical device may be determined and communicated to the medical support network in an emergency. Emergency response teams can be dispatched to the determined patient location with the necessary information to prepare for treatment and provide support after arrival on the scene.

Enhancements available due to technological improvement are included to provide additional benefits to what was available in U.S. Pat. No. 5,752,976 from which these stem.

These improvements include enhancements to the ability to locate the user of the inventive device by dynamic relative location (also called dynamic relative navigation), time slicing of patient device signals to the provider network to improve the normal, non-emergency communications features, clock updating in the patient devices using high accuracy clock signals available from the satellite systems used in GPS which can enhance the fine granularity of available time slicing of patient device communications signals, the use of Enhanced 911 (called E-911, which will permit triangulation on the cell phone callers location through the E-9 11 system) or other emergency telephone systems (including current 911 systems), dead reckoning , improved GPS systems like DGPS, reporting changed location if a larger than some predetermined distance is traversed by the patient device, cell phone triangulation and emergency location, all to supplement contact location information, and the transmission of raw data to be position calculated at remote or emergency vehicle locations.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
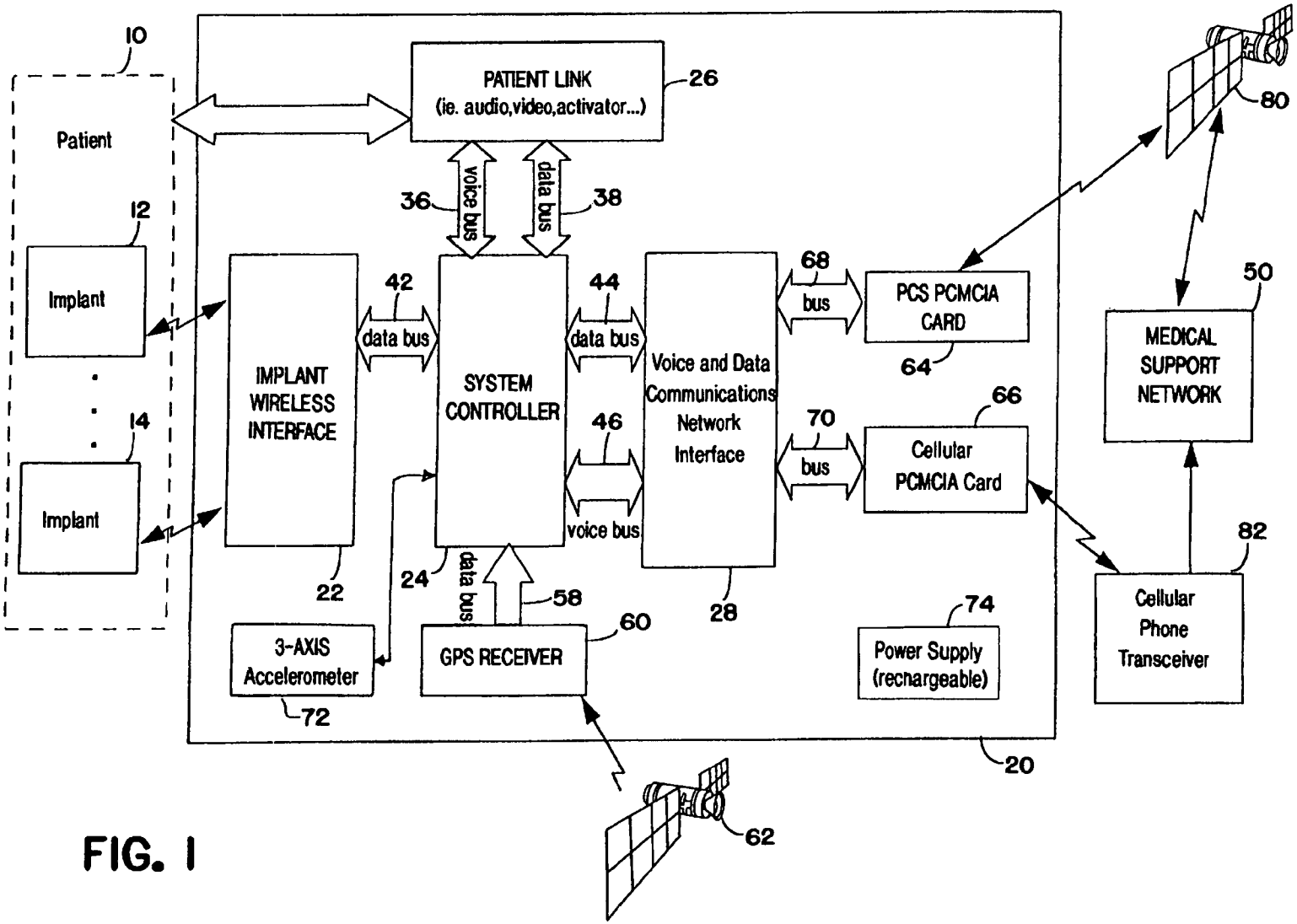
FIG. 1 is block level diagram of a first variation of the system of the invention for a patient having free ranging mobility including an implantable medical device, a patient communications control device and a medical support network optionally employing wireless satellite telecommunication and a global positioning satellite receiver.
Figure 2:
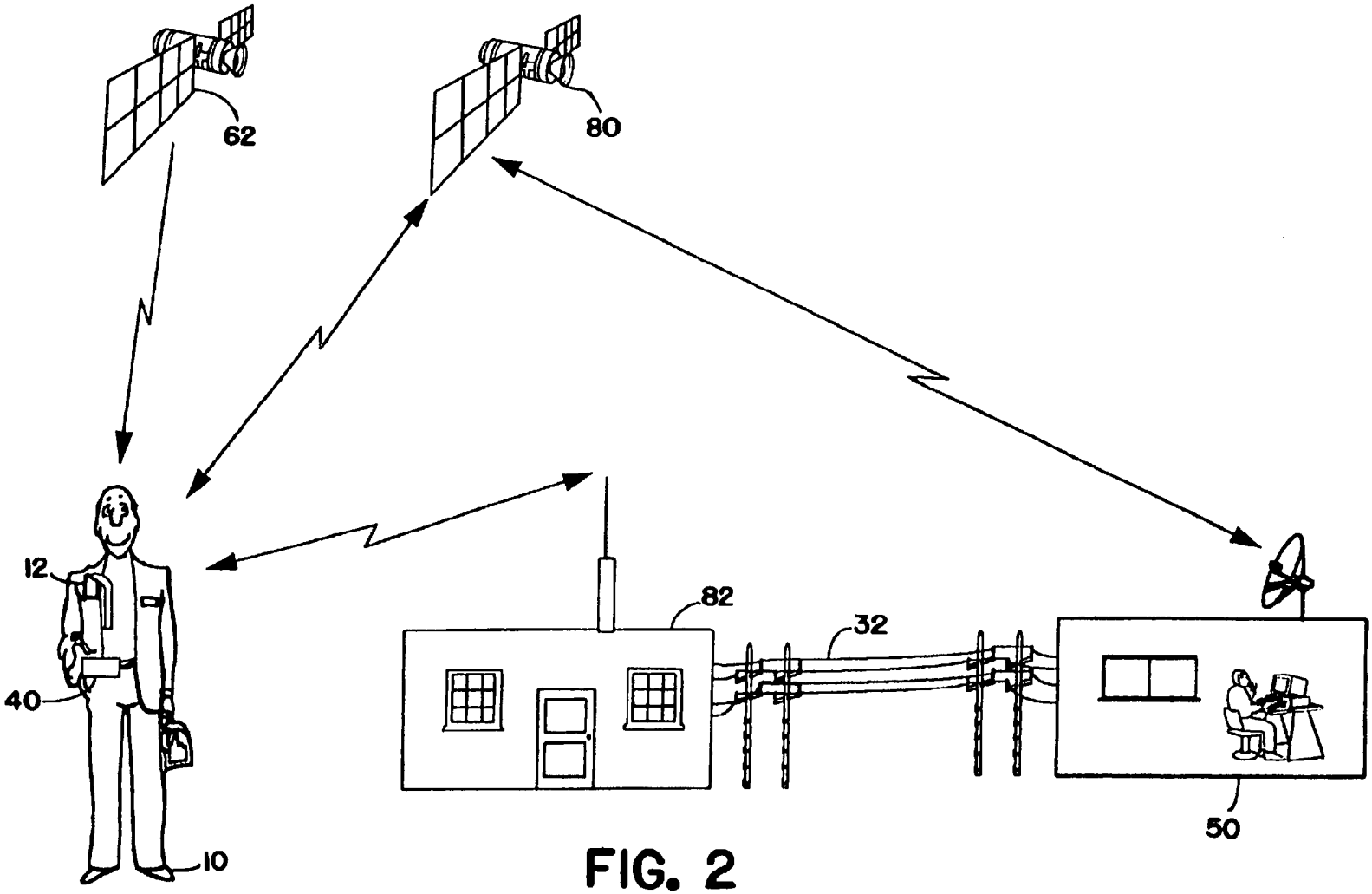
FIG. 2 is a schematic illustration of the system of FIG. 1 in relation to a patient.

The Global Communications and Monitoring System (GCMS) of the present invention provides a means for exchanging information with and exercising control over one or more medical devices implanted within the body of a patient employing the patient communications control device. The GCMS in its most comprehensive form of FIGS. 1 and 2 is intended to function no matter how geographically remote the patient may be relative to the monitoring site or medical support network. In this form, the GCMS provides an alarm to notify the medical support network should device or patient problems arise, determines patient location via the Geopositioning Satellite System (GSS), and allows verbal communication between the patient and monitoring personnel via a cellular telephone system link (if available at the patient location) or a satellite based telecommunications link if the patient is outside the range of a cellular link or subscribes only to the satellite-based link.

Improvements in technology are now available since the filing of the parent applications hereto that allow for enhancement of the features first described. Also, some additional problems and opportunities have been identified and addressed in this application. The improvement in GPS accuracy provided by DGPS systems and the development of cell phone location techniques have provided new opportunities to enhance patient location. The fact that behind some barriers, like trees, buildings, and so forth block some GPS signals has provided the inventor to improve the original disclosure. Likewise, some new thinking about how to improve the ability to find patients, including dead reckoning intelligence being added to the patient devices and use of time slice updates to the medical provider system have increased the usefulness of the invention.

Figure 4:
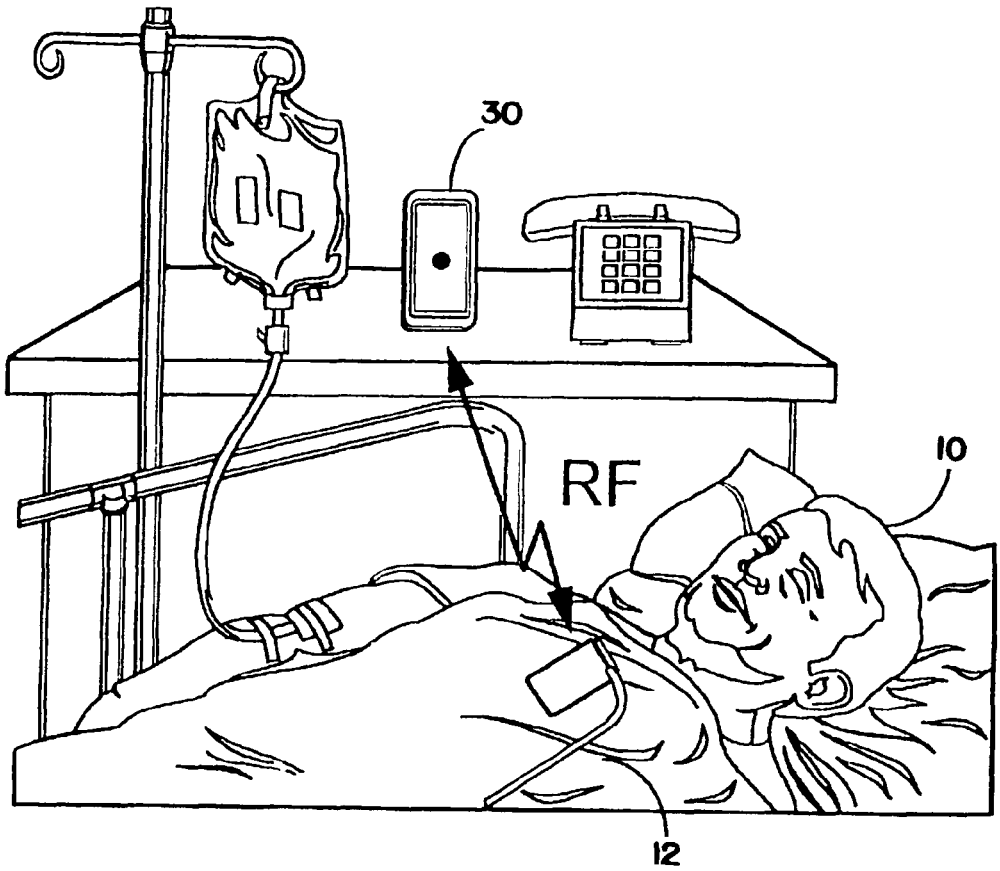
FIG. 4 is a schematic illustration of the system of FIG. 3 in a line powered monitor for use in a patient's hospital room.
Figure 5:
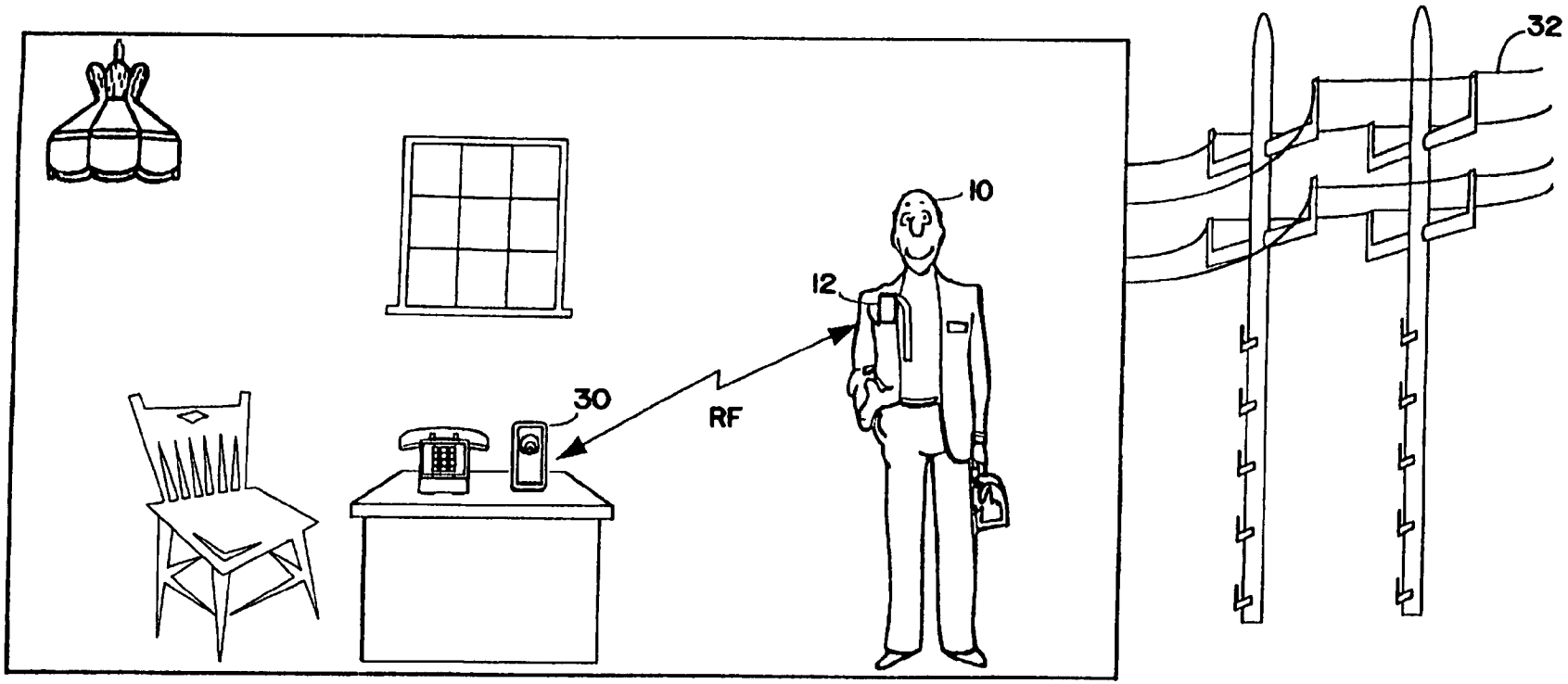
FIG. 5 is a schematic illustration of the system of FIG. 3 employing a patient-worn, communications link and a line powered monitor for use in a patient's home.

The system is not intended to be limited to such remote use by a free ranging patient and is intended to also be used when the patient is less mobile. In the sub-system or second variation illustrated in FIGS. 3-5, the patient communication control device is intended to be coupled to a telephone or other communications system for a patient with more limited mobility. For example, the standard telecommunications system may be accessed either through a hard-wired link or by a cordless telephone with a telephone receiver in the room attached to a phone jack. In this case, the cellular or satellite-based telecommunications interface capabilities are not necessary, and the GSS capability may be superfluous. Preferably, the GCMS of FIG. 1 includes all of these capabilities embodied in a patient communications control device that is small and light enough to be attached to the patient when the patient is mobile or to be used by the patient as a free standing unit at the patient's residence or hospital room. Alternatively, as shown in FIGS. 3-5 the GCMS can be re-configured in part as a stand alone, line powered, room monitor and the remaining part can be implemented as a patient-worn, battery powered, communications link with a transceiver capable of two-way communication between the patient, the implanted medical device and the line powered monitor.

Figure 3:
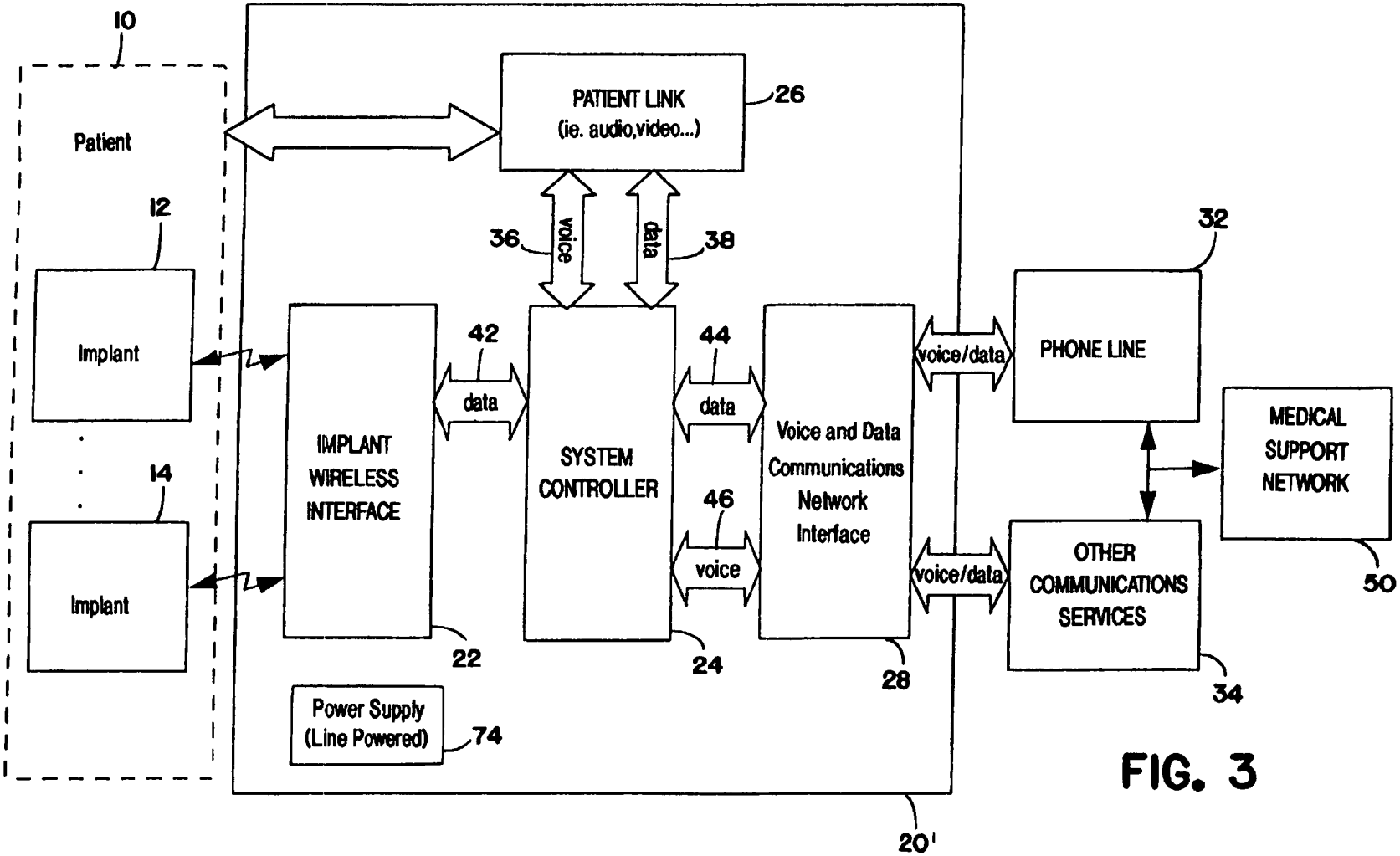
FIG. 3 is block level diagram of a second variation of the system of the invention for a patient having limited mobility including an implantable medical device, a patient communications control device and a medical support network employing conventional wired telecommunication.

FIGS. 1 and 3 are intended to show the alternate components of both of the variations of the GCMS, although the alternate components may be included in the same GCMS. The patient 10 has one or more implanted medical devices 12, 14, which in the latter case may communicate with one another is known as, for example, using the body medium in a manner described in commonly assigned U.S. Pat. No. 4,987,897 to Funke. The medical device 12 (and associated device 14, if present) may be, for example, an arrhythmia control device, e.g. a cardiac pacemaker or a pacemaker-cardioverter-defibrillator. A relatively wide range of device operating modes and parameters are remotely programmable to condition such a device 12 to diagnose one or more conditions such as cardiac arrhythmias and/or deliver electrical or other stimulus appropriate for therapy. The implanted medical device 12 may alternatively be a drug administration device, cardiomyoplasty device, neural stimulator or any other implantable device with electronic control functions that can be programmed and/or have memory for storing patient and device operating data.

At least one implanted medical device 12 possesses a transceiver of the type known in the art for providing two-way communication with an external programmer. The encoded communication may be by the RF transmission system such as is described in the above-referenced '869 patent or by using spread spectrum telemetry techniques described in U.S. Pat. No. 5,381,798 to Burrows or by the system disclosed in the above-referenced U.S. Pat. No. 5,683,432 or any of the known substitutes. The telemetry technique employed and the transceiver of the implanted medical device 12 have enough range to communicate between the transceiver in the implant wireless interface 22 in the remote patient communications control device 20 and the implant (12 . . . 14). The system disclosed in the above-referenced U.S. Pat. No. 5,683,432 may be employed to increase the accuracy and efficiency of the uplink and downlink telemetry.

Figure 6:
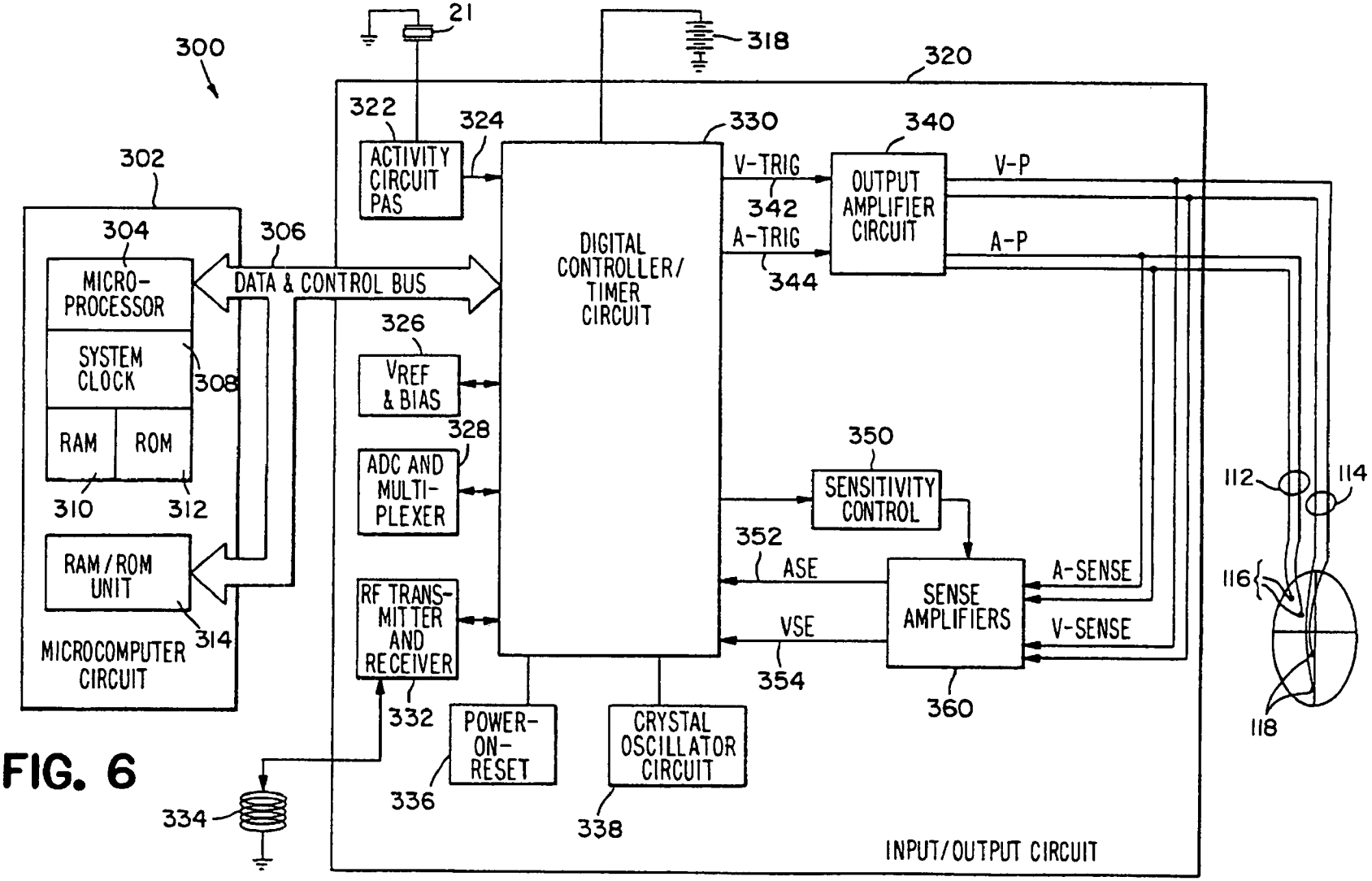
FIG. 6 is a block diagram of an exemplary implanted medical device with which the invention may be practiced.

FIG. 6, depicts an implantable pulse generator (IPG) circuit 300 and atrial and ventricular lead system 112, 114 having programmable modes and parameters and a telemetry transceiver of a DDDR type known in the pacing art as an example of an implanted medical device 12. While described in some detail, this device 12 provides only one example of the kind of implantable device that may be employed with this invention.

The IPG circuit 300 of FIG. 6 is divided generally into a microcomputer circuit 302 and a pacing circuit 320. The pacing circuit 320 includes the output amplifier circuit 340 and the sense amplifiers 360. The output circuit 340 and sense amplifier circuit 360 may contain pulse generators and sense amplifiers corresponding to any of those presently employed in commercially marketed cardiac pacemakers for atrial and ventricular pacing and sensing. The bipolar leads 112 and 114 are illustrated schematically with their associated electrode sets 116 and 118, respectively, as coupled directly to the input/output circuit 320. However, in the actual implanted device they would, of course, be coupled by means of removable electrical connectors inserted in a connector block.

Sensed atrial depolarizations or P-waves that are confirmed by the atrial sense amplifier (ASE) in response to an A-sense are communicated to the digital controller/timer circuit 330 on ASE line 352. Similarly, ventricular depolarizations or R-waves that are confirmed by the ventricular sense amplifier in response to a V-sense are communicated to the digital controller/timer circuit 330 on VSE line 354.

In order to trigger generation of a ventricular pacing or VPE pulse, digital controller/timer circuit 330 generates a trigger signal on V-trig line 342. Similarly, in order to trigger an atrial pacing or APE pulse, digital controller/timer circuit 330 generates a trigger pulse on A-trig line 344.

Crystal oscillator circuit 338 provides basic timing clock for the pacing circuit 320, while battery 318 provides power. Power-on-reset circuit 336 responds to initial connection of the circuit to the battery for defining an initial operating condition and may reset the operative state of the device in response to a low battery condition. Reference mode circuit 326 generates stable voltage and current references for the analog circuits within the pacing circuit 320. Analog to digital converter (ADC) and multiplexor circuit 328 digitizes analog signals. When required, the controller circuit will cause transceiver circuit 332 to provide real time telemetry of cardiac signals from sense amplifiers 360. Of course, these circuits 326, 328, 336, and 338 may employ any circuitry similar to those presently used in current marketed implantable cardiac pacemakers.

Data transmission to and from the external programmer of the patient communications control device of the preferred embodiment of the invention is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarization in the atrium and ventricle, as is well known in the pacing art. The IPG transceiver system disclosed in the above-referenced U.S. Pat. No. 5,638,432 may be employed to provide the uplink and downlink telemetry from and to the implanted medical device in the practice of the present invention.

Control of timing and other functions within the pacing circuit 320 is provided by digital controller/timer circuit 330 which includes a set of timers and associated logic circuits connected with the microcomputer 302. Microcomputer 302 controls the operational functions of digital controller/timer 324, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, ASE and VSE signals. The specific values of the intervals defined are controlled by the microcomputer circuit 302 by means of data and control bus 306 from programmed-in parameter values and operating modes.

If the IPG is programmed to a rate responsive mode, the patient's activity level is monitored periodically, and the sensor derived V-A escape interval is adjusted proportionally. A timed interrupt, e.g., every two seconds, may be provided in order to allow the microprocessor 304 to analyze the output of the activity circuit (PAS) 322 and update the basic V-A escape interval employed in the pacing cycle. The microprocessor 304 may also define variable A-V intervals and variable ARPs and VRPs which vary with the V-A escape interval established in response to patient activity.

Digital controller/timer circuit 330 thus defines the basic pacing or escape interval over a pacing cycle which corresponds to a successive A-V interval and V-A interval. As a further variation, digital controller/timer circuit 330 defines the A-V delay intervals as a SAV that commence following a sensed ASE and a PAV that commences following a delivered APE, respectively.

Digital controller/timer circuit 330 also starts and times out intervals for controlling operation of the atrial and ventricular sense amplifiers in sense amplifier circuit 360 and the atrial and ventricular amplifiers in output amplifier circuit 340. Typically, digital controller/timer circuit 330 defines an atrial blanking interval following delivery of an APE pulse, during which atrial sensing is disabled, as well as ventricular blanking intervals following atrial and ventricular pacing pulse delivery, during which ventricular sensing is disabled. Digital controller/timer circuit 330 also defines an atrial refractory period (ARP) during which atrial sensing is disabled or the ASE is ignored for the purpose of resetting the V-A escape interval. The ARP extends from the beginning of the SAV or PAV interval following either an ASE or an A-trig and until a predetermined time following sensing of a ventricular depolarization or triggering the delivery of a VPE pulse as a post-ventricular atrial refractory period (PVARP). A ventricular refractory period (VRP) may also be timed out after a VSE or V-trig. The durations of the ARP, PVARP and VRP may also be selected as a programmable parameter stored in the microcomputer 302. Digital controller/timer circuit 330 also controls sensitivity settings of the sense amplifiers 360 by means of sensitivity control 350.

The illustrated IPG block diagram of FIG. 6 is merely exemplary of one form of an implanted medical device 12 having a telemetry transceiver. The telemetry transceiver 332 is capable of receiving interrogation commands for uplink telemetry of accumulated data, e.g. stored histograms of intracardiac electrograms (IEGM) or other electrogram (EGM) data maintained in RAM 310 or RAM/ROM unit 314, or of real-time data, e.g. the raw EGM of the patient's heart. In addition, it is capable of receiving permanent reprogramming commands or certain temporary programming commands for changing operating modes or parameters of the IPG 300 to counter a condition diagnosed by the medical support network. In this manner, the selective initiation of the operation of the therapeutic treatment (pacing for device 12) and monitoring can be effected through operating commands received by said implanted device telemetry transceiver 322. Furthermore, the operating algorithms governing the various pacing modes or parameters of those operating algorithms may be re-checked and altered through downlink interrogation and re-programming. In addition, the normal, periodic follow-up of the IPG 300 operation can be remotely initiated and conducted using the uplink and downlink telemetry between the transceiver 332 and the implant wireless interface under the control of the system controller as described below. The present invention can therefore readily be practiced using the basic hardware of existing microprocessor-controlled, dual chamber pacemakers, pacemaker-cardioverter-defibrillators and other medical devices, with a transceiver capable of uplink and downlink telemetry at a distance of up to several meters between the telemetry antenna 334 and the external telemetry antenna of the patient communications control device 20 or 20' of the variations of the present invention.

Returning to FIGS. 1 and 3, the patient communications control device 20, 20' therefore includes the implant wireless interface 22 that operates as a two-way telemetry transceiver for communicating with the telemetry transceiver of the implanted medical device 12 or devices 12, 14 and is controlled in those operations by a microcomputer-based system controller 24, preferably a 486XX microprocessor with RAM and ROM, e.g. the Cardio 486 available from SMOS SYSTEMS located in San Jose, Calif. maybe employed as the controller 24. The system controller 24 contains a system clock for maintaining an accurate time base which in one embodiment may be recalibrated periodically via accurate clocks in the GPS satellites 62. The microcomputer-based system controller 24 is coupled to the patient link 26 and the voice and data communications network interface 28 via voice and data buses 36 and 38. A patient link 26 provides a microphone and speaker through which the patient 10 can use for voice communication through the system controller 24 and the voice and data communications network interface 28 with the remote medical support network 50. Communication between the system controller 24 and the communications interface 28 is via data and voice buses 44 and 46. The system controller 24 may be part of a standard or modified cellular telephone or other personal communication device and may simply recognize specific telemetered signals from the implanted device if desired.

Figure 7:
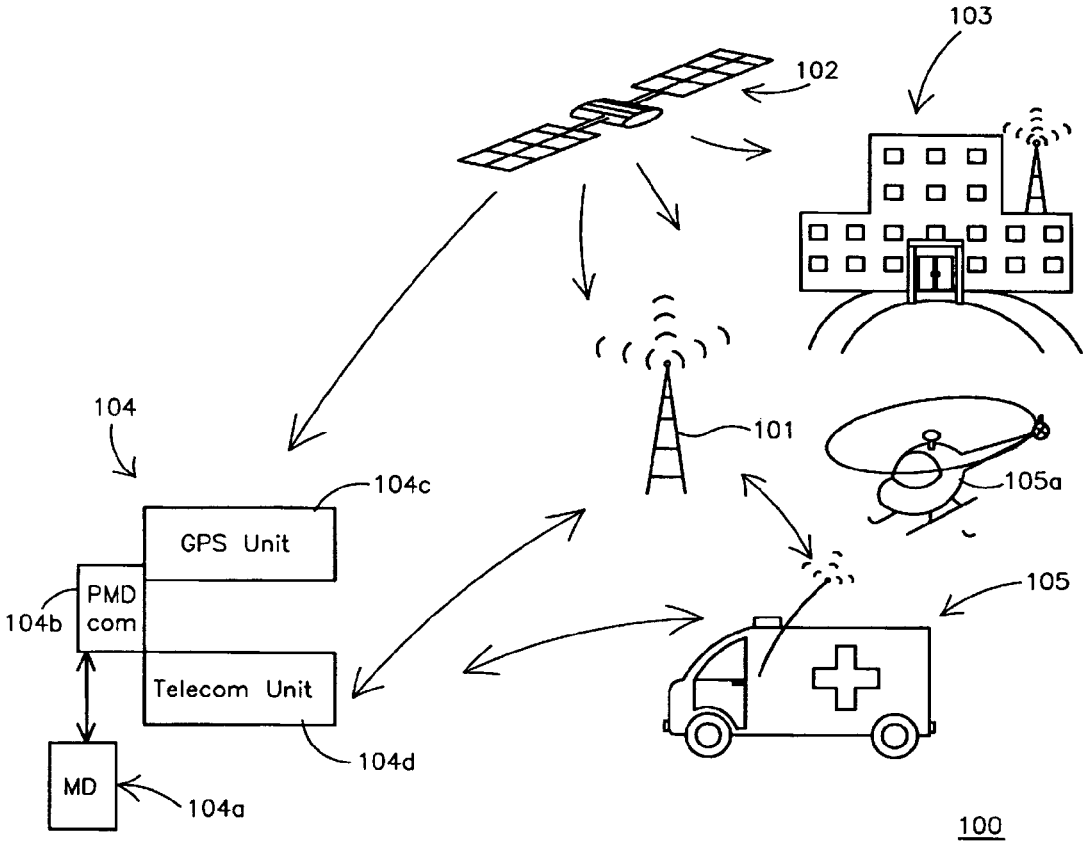
FIG. 7 is a schematic diagram of the main component communicating parts for preferred embodiments of this invention.

At the medical support network 50, a base station is provided to be in the communication link with the monitor 30 or the patient-worn communications device 40. The base station is preferably a microprocessor-based system that includes the software and hardware needed for voice communication with the patients to locate the patient and to interrogate and program the implanted medical devices using the communications interface links incorporated into the GCMS. Alternatively, a system can employ a device similar to the base station as a mobile unit in an emergency vehicle like an ambulance or helicopter as illustrated in FIG. 7, vehicles 105 and 105a. This mobile unit being tasked to find the exact location of a patient in an alarm condition and to rapidly administer medical aid and provide transportation to the most appropriate medical center. Patient voice communications through the patient link 26 include both actual patient voice and/or manually actuated signaling which may convey an emergency situation. For example, a patient may initiate communications through link 26 by depressing a button and/or speaking into the microphone/speaker. The patient voice is converted to an audio signal, digitized, encoded and transmitted either by voice bus 36 or by a transceiver in the case where the patient link 26 is physically separated from the system controller 24, as described below. The patient activated emergency signal is likewise encoded and transmitted by data bus 38 or its equivalent transceiver encoded RF signal to the system controller 24.

Patient link 26 is a custom designed circuit that preferably has a microphone and speaker, associated drivers, a visual indicator (i.e. light or LCD display), and a patient activator. In the embodiment where the patient link 26 is physically part of the patient communications control device 20, the patient link also includes interface circuitry to buses 36 and 38 as shown in FIG. 1. Alternatively, the patient link 26 can be combined with the implant wireless interface as a combined PCMCIA (or other communications) card and a single data bus may be shared between the two circuits. In a further embodiment having a physically separated and separately powered patient communications control device 26, the voice and data buses 36 and 38 can be replaced by short-range wireless LAN PCMCIA cards at each end of the link. An infrared wireless LAN PCMCIA adapter with an integrated transceiver, Model No. 87G9743, is currently available from IBM, Inc., Somers, N.Y. An RF wireless LAN PCMCIA adapter with an integrated transceiver, Model No. 80G0900 is also available from IBM, Inc., Somers, N.Y. Other similar devices may be used. Much improved location finder systems are available from Trimble Navigation and Leica as described below, and these could of course be used to effectuate the improved location of and contacting of the patient system. For most situations basing the receiver on the DGPS in the AgGPS 132 from Trimbal would be sufficient, but including the signal interference capabilities of the 400 rsi and Dsi devices may prove advantageous. By incorporating or using these or even the Leica systems now available to determine location to a claimed 1 cm accuracy, sending the location information from the patient to the emergency locator vehicle could aid in locating a patient more quickly by indicating the direction and distance to that location in the emergency vehicle's base/mobile station display(one example illustrated in FIG. 8. (Citations for Trimbal and Leica are near the end of this application).

Continuing specifically with the first variation of FIGS. 1 and 2, these figures depict the components of the more comprehensive GCMS of the present invention for allowing greater patient mobility, a wider range of communications network interface links and the capability of locating the patient anywhere in the world. In the GCMS of FIG. 1, all components of patient communications control device 20 are incorporated into the patient-worn communications device 40 which may be worn, for example, on a patient's belt or carried in a pocket, or worn on a wrist. Alternatively, as described above, the patient link 26 may be separated into a wrist-worn device having a separate transceiver for convenience of use in voice communication. In any event, the emerging Personal Communications System (PCS) technology may be employed in the miniaturization of the system components.

In accordance with one aspect of the invention, the system controller 24 is coupled to a GPS receiver 60 via bus 58 for receiving patient positioning data from an earth satellite 62. The GPS receiver 60 may use current systems such as the Mobile GPS™ (PCMCIA GPS Sensor) provided by Trimble Navigation, Inc. of Sunnyvale, California or Retki GPS Land Navigation System provided by Liikkura Systems International, Inc. of Cameron Park, Calif., or other similar systems. The GPS receiver 60 may be actuated by a command received through the system controller 24 from the medical support network, in the case of an emergency response. In the case of a non-emergency, periodic follow-up, the GPS receiver 60 may be enabled once an hour or once a day or any other chosen interval to verify patient location. The determined location may be transmitted to the medical support network and/or stored in RAM in the system controller 24. To maintain patient location information in the absence of GPS signals (such as inside metal buildings), a three-axis accelerometer 72 or other position/motion determining device can be incorporated into the system. By knowing original position (from the last valid GPS point), time (from the internal clock) and acceleration (motion), patient position can be calculated from the three axis coordinates realized from each accelerometer output calculated in each case from:

$$x(t)=x(0)+v(0)t+\iint a(t)dt$$

where x(0) is the initial position stored in memory for each axis, t is time, a is acceleration and v is velocity.

In the free ranging embodiment of FIGS. 1 and 2, two communication network interface links with the medical support network 50 are included, although the communication interface links of the second variation of FIGS. 3-5 may be included for optional home use. One non-hard-wired communication interface link is effected through the soon to be deployed, worldwide satellite communications system, called "Iridium", by Motorola, Inc. of Schaumburg, Ill. This is a PCMCIA card 64 which may be built from common components by one skilled in the art. Another (second) communications link can be effected by the ARDIS (Advanced Radio Data Information Service) pocket radio communications network via PCMCIA link card 66, a Mobidem modem available from Ericsson, Inc. of Raleigh, N.C. Both of the radio links operate as modems with voice and data simultaneously transmitted via adding the CT8020 (DSP Group of Santa Clara, Calif.) to a standard data modem such as a 28.8 Keepintouch™ Express modem from AT & T Corp. of Largo, Fla.

Either or both PCMCIA cards 64 and 66 may be provided and they are coupled with the voice and communications network 28 via buses 68 and 70, respectively. When both are provided, access to the communications satellite link 80 is automatically obtained when a link to a cellular transceiver 82 is not possible.

It should be noted that "Iridium" manages cellular location of each subscriber in the network at all times. The subscriber unit, which in this invention would be incorporated into the device 20 (or communicatively connected to it) identifies itself and its location on a periodic basis to the system manager. In any system chosen it is expected that the control and communications device will have to report in to a management system regarding its location on a periodic or at least on a changed location basis or both. The implanted device need not be concerned about this activity and need not use any of its battery power to accomplish it since only the external device 20 (in the preferred embodiments) needs to be involved in such location communication. Only by knowing the patient location can the medical system 50 communicate to the implanted device at any time it wants or needs to. Accordingly, if emergency communications are expected short intervals between reporting in are recommended.

By checking in, the patient's external communications device would act like a cellular phone, answering incoming medical system messages broadcast into the cell in which it is located.

For patient convenience, a personal communicating device may incorporate the controller/communicator that communicates between implanted device(s) and the external world. In this way it could look like and operate as a personal communicator or cellular phone and reduce patient psychological discomfort. It should also be recognized that if the cellular telephone system manages all communication functions between the outside-the-patient-system and the medical community system, the implanted device need only be able to communicate with the cellular communications product.

FIG. 2 illustrates the free ranging patient 10 located remotely from the medical support network 50 and from any hard-wired communications link. The patient communications control device 20 is implemented in the belt-worn portable unit 40, although the patient link 26 may be worn separately on the patient's wrist (not shown). Alternatively, the patient communications control device 20 including the patient link 26 may be packaged into a portable telephone configuration and carried in a pocket. In any embodiment, the patient location may be determined by communications with the GPS 62. The voice and data communications link with the medical support network 50 may be effected by a cellular phone link including transceiver 82. Alternatively, the voice and data communications link may be effected using the communications satellite link 80.

The patient communications control device 20 of FIGS. 1 and 2 is powered by a battery power supply 74 that preferably is rechargeable, or alternatively by commonly available batteries of any type. The system controller 24 includes a power control system for powering down the microprocessor and the associated components of the patient communications control device 20 except on receipt of an interrupt in a manner well known in the art.

Power consumption can be significantly reduced by powering up the communication and satellite circuitry periodically for a short period of time to re-acquire a GPS location and/or look for requests for data or status from the medical support network 50. This system power consumption reduction can greatly enhance battery lifetime requiring less frequent battery replacement or recharging, in the case of a rechargeable battery configuration. As an alternate to using a management system to maintain a patient location data based on patient's device periodic check-in each GCMS system for each patient could have a specific time slot (for example, 30 seconds) non-overlapping with other GCMS systems to power up, acquire location coordinates from the GPS system and be alert for a call from the medical support network 50. Periodically (for example, once per day), the medical support network 50 would reset/recalibrate the system clock in system controller 24 from the atomic clock in the GPS satellite system. This would ensure that no specific GCMS system clock would drift out of range of its allotted time slot and be unavailable for reception or drift into an adjacent time slot. Other time dividing schemes used in other arts may also be employed to maximize battery life for any system.

Time slicing the power up communications can increase the number of available time slots in a local system if the time slices are small and accurately maintained. To do this, the patient's system would simply update it's internal clock with reference to the atomic clock signal broadcast via the satellite to maintain accurate timekeeping for itself.

Turning to the second variation of the invention illustrated in FIGS. 3-5, it should be noted that the system of FIG. 1 may also be used in the home or in the hospital using the cellular communications link card 66. However, the modified patient communications control device 20' of FIG. 3 is preferably implemented with the voice and data communications network interface 28 having the capability of directly linking with a hard-wired phone line 32 or other communication services, which may include a hospital installed network, e.g. a personal computer interface to a local area network. In either case, the modified patient communications control device 20' may be implemented in a number of portable or stationary monitor 30 forms.

In the embodiment illustrated in FIG. 4, all of the FIG. 3 components of the modified patient communications control device 20' are located in the monitor 30. The patient link 26 and the implant wireless interface 22 are hard-wired by voice and data buses 36, 38 and 42 to the system controller 24. In the embodiment of FIG. 5, the patient link 26 and the implant wireless interface 22 are located in the patient-worn communications device 12. The remaining components of the modified patient communications control device 20' are located in monitor 30, and suitable RF telemetry transceiver links are substituted for the buses 36, 38 and 42. In either embodiment, the power supply 74 of the monitor 30 may be line powered. The modified patient communications control device 20' within monitor 30 may also be coupled to a wall jack for hard-wired communications through the phone line 32 or other communications service 34 with a medical support network 50 located remotely or within the hospital.

As described above, implantable devices such as 12 . . . 14 include telemetry transceivers with range suitable for communicating over a short range to the implant wireless interface 22 of the modified patient communications control device 20' within stand alone monitor 30. This remote link offers advantages over patient-worn electrodes or programming heads required in the standard skin contact telemetry and monitoring used at present. Skin contact is difficult to maintain, as the adhesive for the electrodes or heads fails in time, skin irritation is often a problem and inadvertent removal of electrodes is also prevalent. Moreover, the EGM and other body condition monitoring capabilities of advanced implanted medical devices can be taken advantage of to substitute for in-hospital monitoring, e.g. Holter monitoring of the patient's electrogram. The electrogram and/or other sensor derived data, e.g. pressure, temperature, blood gases or the like, stored by the implanted device can be transmitted out continuously or on periodic automatic telemetry command and sent by the communications link to the remote or hospital medical support network 50.

In either environment of FIG. 4 or 5, the patient 10 may communicate with the medical support staff at the medical support network 50 through the voice channel provided in the patient link 26. The patient communications control device 20 or 20' in either embodiment can retrieve all implanted device stored patient and device operating data on receipt of a command from the medical support network 50, process and temporarily store such data, and transmit it back to the support network 50 for analysis. Moreover, implanted devices 12 . . . 14 may be reprogrammed from the medical support network 50 to alter device operating modes and parameters employing the modified patient communications control device 20' as a programmer. Finally, the modified patient communications control device 20' can transmit an alarm to the medical support network should there be problems with the patient or implanted devices 12, 14. For example, the implanted devices 12, 14 may signal a low battery condition or a low drug supply in the case of an implanted drug dispenser or other problems found in self-diagnostic routines periodically conducted within the implanted devices 12 . . . 14.

The variations and embodiments of the GCMS of the present invention provides comprehensive monitoring of implanted medical devices independent of the geographic mobility of the patient using the devices, obviating the need for the patient to return to a designated follow-up monitoring site or clinic. Moreover, it allows determination of the patient's geographic location via the GSS 62 while providing simultaneous two-way communication with devices and the patient when desired. In addition to emergency response and routine patient management, the GCMS facilitates medical device clinical studies, providing data collection at one central site from all study patients without requiring their active involvement or clinic visits. This is especially useful for conducting government-mandated post-market surveillance studies. Should there be need to upgrade or change the behavior of implanted devices the global system allows a central monitoring site to revise all involved implants anywhere in the world by transmitting new programming instructions to every device (assuming appropriate governmental authorities and the patients' physicians have agreed to the need for such changes). The patient need not be directly involved in this updating and need not be aware of the actual process.

A continuous and automatic medical monitoring service could be implemented to shorten response time for emergency medical situations or device events signifying patient difficulty. For example, a patient having an implanted cardioverter/defibrillator may be subjected to multiple defibrillation shocks, due to an underlying arrhythmia that cannot be converted by the shocks. To achieve this in the first variation of FIGS. 1 and 2, the implanted medical device 12 or 14 would initiate an emergency transmission to the patient communications control device 20 which would contain, but not be limited to, all or some of the following: patient name and mailing address, patient's current location, patient's current medical condition requiring assistance, ongoing "real time physiological variables", patient medical support team information, and current status (patient and device) and data stored within the implanted medical device. The patient communications control device 20 would obtain the GSS signal and transmit all the information to the medical support network 50. The patient may also transmit voice information if conscious of the event. A similar response to an emergency situation can be initiated and completed in the GCMS of the second variation using the modified patient communications control device 20'. And, as mentioned before, the time slice can be very small for each patient in a local provider network if the system checks its time clock against the atomic clock time signals available from the satellite.

Moreover, patient follow-up and periodic monitoring (i.e. monthly, quarterly, etc.) of the medical implant's stored data and status could be done automatically and be completely transparent to the patient. The medical support team would even have the capability of changing the implanted device settings or programming with complete transparency to the patient (or alternatively, voice or warning signals may be used to identify impending programming).

Interactions with the implanted device and patient may be totally transparent to the patient, e.g., routine location checks to determine if the patient is in proximity sufficiently with the patient communications device to interrogate the implanted device or for follow-up data collection from the implanted device's monitoring memory or reprogramming of operations of the device effected at night while the patient sleeps. Or the patient may be included in the process, even to the extent that voice communications from the staff at the support network to instruct or reassure the patient are received in the patient communications control device.

The following chart details the communications pathways and the data that can travel over them are detailed in the following chart.

| | |
|---|---|
| Medical Device(MD) Data to Belt Device | a. Serial No. or other unique ID data<br>b. Patient Condition<br>c. Device status data<br>d. Device Sensor data<br>e. Coordinating data |
| Belt Device to Medical Device(MD) | a. Commands to MD(change a program parameter/value/sequence, interrogate, request a program or data, etc.)<br>b. Coordinating data (ex. outside pressure) |
| Network Data to Belt Device | a. Commands to Belt Device or MD<br>b. Coordinating data(ex. DGPS) |
| Belt Device to Network | a. Belt Device data (which includes all data from the MD and Belt Device generated data including Dynamic Relative Reference, and GPS and DGPS as required or requested.) |

NOTES:

Wake-ups, acknowledgments, protocol, error correcting, and handshaking all as designed for each component to component communication. It should be noted that Network includes for example any number of nodes in a telephone system that are part of the health care provider network, or any specific one of such nodes.

Using these communications features we can enhance the functionality available to the medical community for using these devices, while at the same time providing enhanced location of patients in emergency situations.

In particular, we use the enhancements of the GPS system called DGPS to more accurately identify the patient location.

We also use on-board automatic dead reckoning facilities in the belt worn or in the IMD itself to provide update control and location information relative to a last DGPS or GPS location. We also can provide interaction with cellular telephony systems that can now be used to provide location information as well.

To reduce the amount of information processing that has to be done in the belt worn or IMD, we can take advantage of the nature of the GPS data itself. This data can be represented as follows. The table illustrates a variable length data transmission from the patient communications control device 20 (or 20') to the remote medical support network 50, for example.

DATA TABLE:

| Byte | Label | Description |
|---|---|---|
| 0 | Sync flag | A hex value to identify the start to receiver (usually FF) |
| 1-2 | Length of Data | integer indication of number of bytes to follow |
| 3-6 | Patient ID code | Unsigned long integer value |
| 7-8 | GPS FOM | Figure Of Merit, calculated by GPS (integer value, depends on number of satellites in view) |
| 9-10 | GPS GDOP | Geometric Dilution of Precision calculated by GPS (integer value, includes the time correction data based on the satellite broadcast atomic clock data) |
| 11-18 | GPS Latitude | IEEE double precision format |
| 19-26 | GPS Longitude | IEEE double precision format |
| 27-n | ECG/physiologic signal/device status, etc. | number of bits dependent on digitization rate and what data is being sent |
| n + 1 | LRC | Longitudinal Redundancy Check data and ECC data to correct errors in transmission. |

When using the system to locate patients, the Contact Patient software module contains two identical arrays that form the binary data packets. While one packet is collecting real time data from the ADC 328 of implantable device 300 and the result of a GPS calculation, the other is communicating to the base station. Once every second the packets change function (commonly called double buffering). Real time displayed data is delayed by one second. The actual data transmission time depends on the amount of data, which is set by the digitization rate and the baud rate achieved over the wireless link between devices. Typically the table full of data would be transferred in a third of a second.

Alternatively, to save power in the patient worn belt and IMD devices, the use of the GPS Latitude and Longitude calculations need not be made. These could be calculated in a computer in a rescue vehicle (FIG. 7 ) or in the hospital, or somewhere else in the system, from raw GPS satellite data and thereby saving power for the small devices. Simply turning off the main GPS receiver activities will save power too, as was demonstrated in U.S. Pat. No. 5,592,173, incorporated herein by reference. In this patent as well, a dead reckoning system is also suggested as being useful in the powered down mode.

Referring now to FIG. 7, in which a system 100 in accord with one aspect of this invention is shown, a tower 101 base station, broadcasts its correction data from its known location to the devices located in a clinic/hospital 103, a moving rescue vehicle 105 and the patient system 104. There currently are at least two DGPS systems commercially available, one form Trimble Navigation Limited, Sunnyvale Calif. and Hampshire England, and another from Leica Navigation and Positioning of Torrence California and Leica Inc., Norcross Ga. Both these companies provide base stations for broadcasting and receivers for receiving and correlating GPS and DGPS data that could be useful for the system components shown in FIG. 7, but other similar systems could be used as well. A description of the features providing for DGPS location in the Trimble system are mentioned in the U.S. Pat. Nos. 5,777,580, 5,745,868, 5,731,768, and 5,680,140, all of which are herein incorporated by this reference.

The satellite 102 could be any of the GPS satellites, and the hospital or clinic 103 could be any medical facility. The personal system of the patient 104, may be worn for example on a belt or pendant or by other means kept near his body, as preferably two parts, the medical device MD (104a) and the belt worn device consisting of the programmer type communicating module PMD 104b for communicating with the medical device 104a, the telecom unit 104d for communicating with local telephony systems through wireless cell phone type technologies, and the DGPS or GPS unit 104c, which receives the satellite data and data from fixed base stations like station 101.

Figure 8:
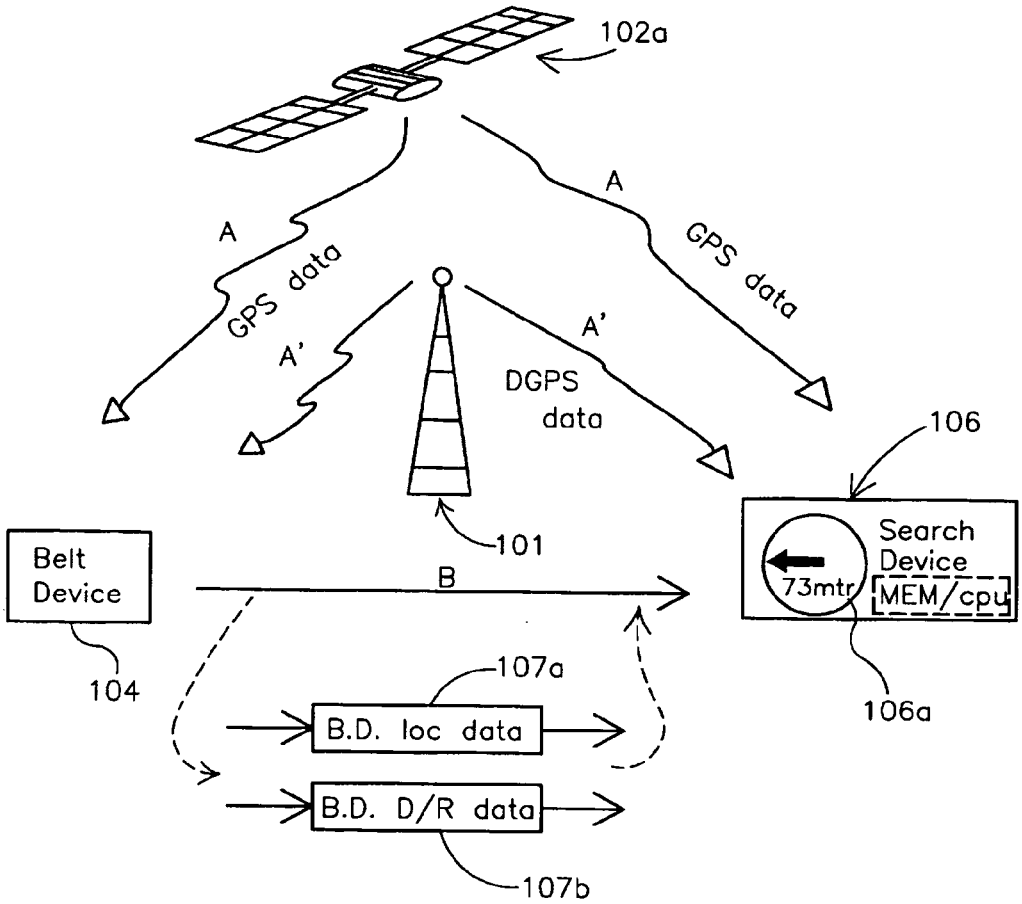
FIG. 8 is also a schematic diagram of the main component communicating parts for preferred embodiments of this invention, as adapted to help in quick location of patients.

Referring now to FIG. 8, the belt worn device 104 receives satellite data A, broadcast from a set of satellites 102a-n (only one is pictured). It also receives broadcast correction data signals A' from a base station 101. The finding system in device 106 receives this same data. When alerted to be looking for the location of the patient worn device 104, device 106 will also be looking for information broadcast by device 104 in signal B. Generally this data will include information received from the satellites 102a-n that are in range of the belt worn device 104 in a packet 107a and the correction data received from the DGPS base station 101 in packet 107b. From this data the exact location of device 104, can be computed. By computing this location data itself, device 106 can then compute its own location and produce a vector to the device 104 for display (like display 106a) to the user of device 106. It is believed that the most effective display would be a directional arrow with a numeric display of distance units to the device as illustrated, but any combination of numeric, alpha, and illustrative displays as well as audible signaling including speech (for example, the device could say 20 yards to your left for use by a fire fighter in a smoky building) may be used if desired. There is also no reason not to incorporate a telephone receiver for direct communications with the patient in both the devices 104 and 106 if desired.

The data in the interchange between the mobile finding device 106 and the patient belt worn device 104 can be in many forms, but preferably we would use a data format like in the DATA TABLE, above.

Improvements in the flexibility of how to access a patient in distress or for location of any other person using a device such as 140 in FIG. 8 can be had using alternate systems already in use.

For example, in the United States, there is a new FCC proposed rule for broadband personal communications services carriers to comply with section 103 of the Communications Assistance for Law Enforcement Act, so many competing systems for location of cell phones will be available to supplement the finding features of this invention. It is believed that nearly all cell phone systems will be able to locate their users within 15 meters under this initiative. While this initiative is related to law enforcement activities primarily, it's use for medical emergencies should not be proscribed. There is also an initiative to have emergency calls to the Emergency 911 (E911) system from cell phones activate location information for the emergency response services to be more effective. Finally, if the medical device (104a of FIG. 7) notes that its wearer has an emergency condition, it could activate a call by a communication to the PMD corn unit 104b to call the 911 or other emergency service (using unit 104d) through the wireless telephone system. An initial location data stream would preferably automatically be sent with the initial call when the call was made, using this new initiative system. This information receiving function could be incorporated into emergency telephone receiving equipment or if the emergency services don't provide it, a voice transmission of the nature of the emergency and perhaps some indication of location could be given by the telecom unit 104d from a bank of recorded message parts to emergency response personnel. If special equipment is incorporated in the emergency telephone communications system, emergency codes could be sent along with the location data or just sent by itself. Also, code data regarding the patient condition, like blood pressure, temperature, battery fault in an implanted device or any other relevant information regarding the patient condition, environment or device status can be reported with the emergency coding.

Time slice updating of the status of a device like that of 104 in FIG. 8, implants 12, 14 etc. and 20 of FIGS. 1, or 12 and 30 of FIG. 2, can be effectively provided to many thousands of patients in a geographic region with little difficulty provided there is accurate keeping of time by all units in a given system.

Figure 9:
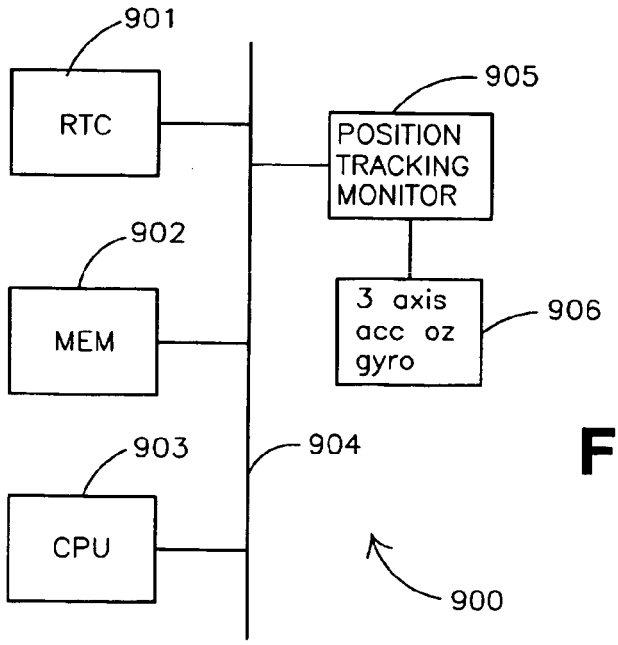
FIG. 9 is a block circuit diagram of components useful for maintaining a relative to last GPS address location, in accord with a function of this invention.

FIG. 9 illustrates the main internal components needed for keeping track of the patient location if the GPS system is temporarily unavailable, and for using a dead reckoning system to complement the GPS or DGPS systems in any other ways. There should be a real time clock 901, a microprocessor unit 903 and some memory circuits 902 connected by circuit lines or a bus 904 to the position tracking monitoring circuitry 905. This tracking and monitoring circuitry should also be associated with a gyroscope like device, a minimized inertial navigation system, a multi-axis accelerometer system, or some other mechanism useful to track the movement of the patient in three dimensional space. A number of different systems have been worked out that would be satisfactory for this purpose, and any of these could be chosen. The inertial navigation systems used in modern aircraft provide other examples. Alternatively, the pedal impacts based system described in U.S. Pat. No. 5,583,776, hereby incorporated by reference may be used. This will allow for patient location when out of the range of GPS systems and also for rapid restart upon re-entering the GPS or DGPS fields instead of a 10 minute "cold start" which would otherwise be required.

An additional feature this inertial navigation system can provide is to initiate a transmission to the provider system in the event the patient moves greater than a set distance, say 100 yards. The supplementation of a dead reckoning system beyond the DGPS or GPS provides for a second source for checking whether the patient has moved so the device should function through a GPS outage. Such a system could keep track of Alzheimer's patients with minimal supervision, for example.

Because of its current level of accuracy, wherever we can we would prefer to rely on the data from the modern DGPS systems for dynamic relative navigation. Examples of systems currently taught include those described in U.S. Pat. No. 5,689,431, and U.S. Pat. No. 5,680,140, and U.S. Pat. No. 5,583,517, all incorporated herein by this reference. Triangulation techniques of U.S. Pat. No. 5,784,339, and spread spectrum techniques of U.S. Pat. No. 5,583,517, both also incorporated by reference, may also be used if desired.

Figure 10:
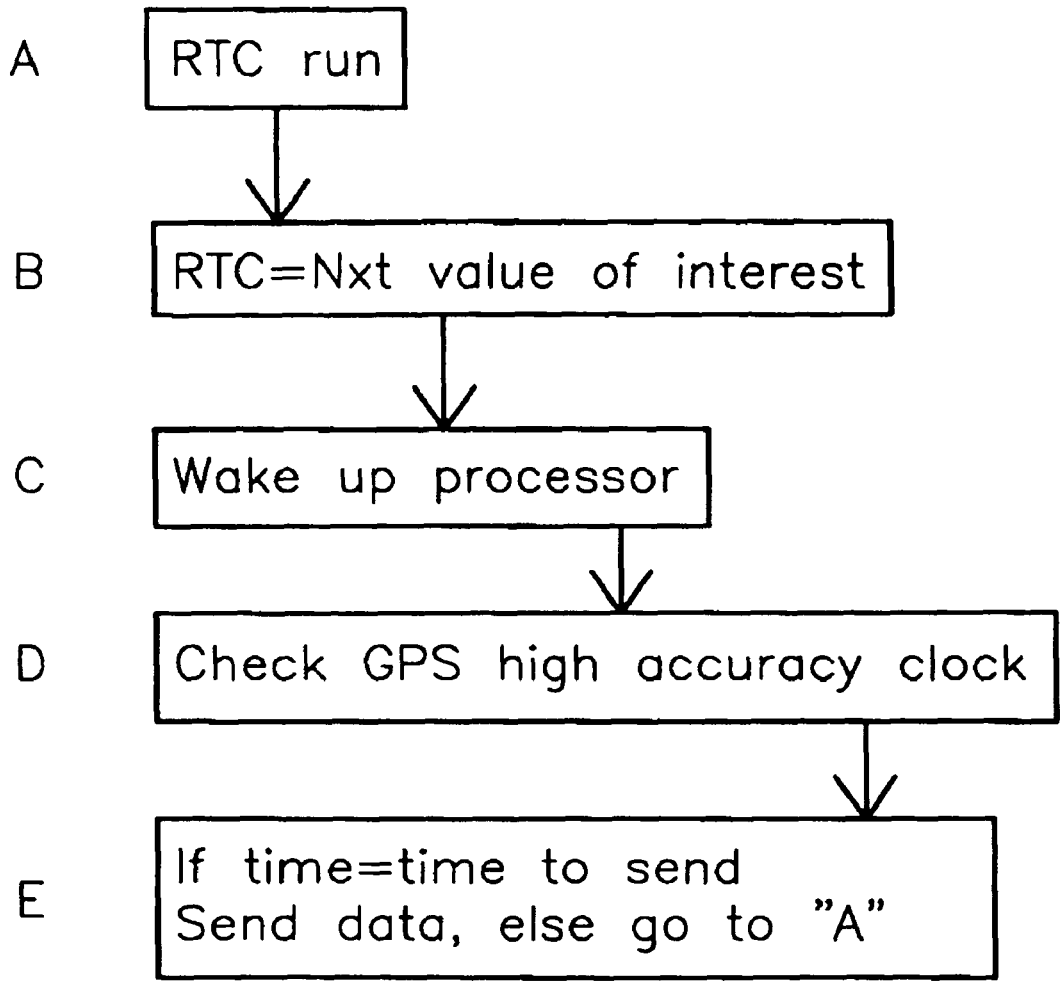
FIG. 10 is a flow chart of steps for coordinating time slice reporting of device status in accord with a feature of this invention.

FIG. 10 illustrates the method by which the system of FIG. 9 may be called upon to work. In step A, the real time clock is running, until at step B it is recognized that the real time clock is at the next time value of interest, that is the next day, hour or minute whenever the system needs to check on its location relative to the last good GPS or DGPS fixation reading. Alternatively, whenever the patient system is supposed to report in to the local medical provider system a real time clock setting can be associated with this step B. In any event, in step C, the processing capability of the system needs to be engaged to do whatever is required.

Step D has the system checking the high accuracy clock for comparison to the running real time clock in the patient local device or devices, such as the system 104 of FIG. 7, for example. If the time is accurate, then the device can simply process as normal, otherwise it needs to update the real time clock(s) it maintains so as to be able to communicate in its proper time slice within the local provider system.

In Step E, the system on the patient needs to check to see if the time from the properly updated real time clock is appropriate for it to send data, and if so, to activate the part of the system that communicates the data to the medical provider system. Otherwise if the time is not right, it can go back to Step A, and let the processor power stay off until the next value of interest is seen from the real time clock. (A description of power cycling to save battery life is found in U.S. Patent No. 5,592,173, incorporated by this reference, and a description of use of this in a vehicle location GPS system is in U.S. Pat. No. 5,777,580, also incorporated by this reference).

For communication between an implanted device and an externally worn patient device, common telemetry techniques presently used by any pacemaker manufacturer may be employed, as well as less evident techniques such as is described in the Funke Body Bus of U.S. Pat. No. 4,987,897, or his acoustic bus, in U.S. Pat. No. 5,113,859, both incorporated herein by this reference.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

I claim:

1. A patient monitoring system comprising:

a transceiver unit to be located in immediate proximity to a patient's body for communicating with a device implanted in the patient's body and with a telephone system outside the patient's body, the transceiver unit comprising, a GPS location system for receiving satellite transmitted information from a set of earth orbiting satellites, an IMD receiving telemetry circuit means for receiving telemetry from said implanted device, a memory circuit for storing data relating to data received from said implanted device and from said earth orbital satellite, telecommunications module for communication through wireless telephonic channels to said telephone system, real time clock circuit producing an output signal for a real time clock, transmission initiation processor for generating an automatic transmission over said telecommunications module through said wireless telephonic channels containing information related through said implantable device to said transceiver unit, said automatic transmission to occur at a set of periodically occurring fixed times, and real time clock circuit update processor for interpreting received satellite transmitted information and providing an update for the real time clock circuit based on said satellite transmitted information so that said transmission initiation processor can operate within an extremely accurately clocked time slice.

2. A patient monitoring and emergency location system comprising;

a patient monitoring system as set forth in claim 1 and further comprising;

circuit means for producing a representation of said received satellite information relating the location of said transceiver unit for presentation to said telecommunications module so that said telecommunications module can transmit said representation of said location information to location receiving means in an emergency response system connected to said telephone system.

3. A patient monitoring and emergency location system as set forth in claim 2 said transceiver unit further comprising;

DGPS receiver means for receiving DGPS signals from a base station, and wherein said circuit means for producing a representation of said received location information for presentation to said telecommunications module is configured to also provide DGPS information to said telecommunications module.

4. A patient monitoring and emergency location system as set forth in claim 2 said transceiver unit further comprising;

dead reckoning circuit means for determining the relative location of said transceiver unit over time to any location at a fixed time during which an acceptable fixed location of said transceiver unit is known, and wherein said circuit means for producing a representation of said received location information for presentation to said telecommunications module is configured to also provide a representation of said dead reckoning information to said telecommunications module.

5. A patient monitoring and emergency location system as set forth in claim 2, said transceiver unit further comprising;

a distance traveled interpretive processor for receiving an output from said dead reckoning circuit and determining a distance traveled therefrom, a trigger circuit for triggering the initiation of transmission to said telephone system by said telecommunications module when the distance traveled interpretive processor determines a distance traveled is greater than a predetermined trigger distance value.

6. A patient monitoring and emergency location system as set forth in claim 2 further comprising a processor adapted for transmitting emergency information from said transceiver unit to an emergency E911 system.

7. Emergency response system for receiving location information from a transceiver unit in proximity to a patient with an implantable medical device in communication with said transceiver unit, said emergency response system comprising;

at least one mobile unit operational on an emergency basis for receiving location information from said transceiver unit and having a GPS system and a computer system therein, such that said mobile unit GPS system produces data related to a present location of said mobile unit and makes said data related to said present location of said mobile unit available to said computer system and said mobile unit computer system comprises processor means for processing said received location information from said transceiver unit and said data related to the present location of said mobile unit to produce an indication of the relative position of said transceiver unit to said mobile unit, and a base station for receiving through a telephone system a current location representation from said transceiver unit along with status information related to an implantable device implanted within a patient associated with said transceiver unit.

8. Method for operation of a transceiver unit for wearing on a person having location means and means for communicating with an implant and with a telephone network comprising:

providing a telemetric communications pathway between an implanted medical device(IMD) and a patient word device(PWD) to facilitate the transfer from the IMD to the PWD of data relating to any of the following information types: a. Ser. No. or other unique ID data, b. Patient Condition, c. Device status data, d. Device Sensor data, and/or e. coordinating data, providing a telemetric communications pathway between an IMD and a PWD to facilitate the transfer from the PWD to the IMD of data relating to any of the following information types: a. Commands and /or b. Coordinating data, providing a telemetric communications pathway between a node on a telephone network and said PWD and between a satellite GPS system and said PWD so as to facilitate the transfer of any of the following information types from said node and/or said satellite GPS system to said PWD: a. Command data and/or coordinating data, and providing a telemetric communications pathway between a node on a telephone network and said PWD so as to facilitate the transfer of any of the following information types from said PWD to said node: PWD device data including any data received by the PWD from the IMD and/or any sensor data that may be developed and stored by the PWD and/or PWD status data and/or Dynamic Relative Reference data from a dead reckoning system associated with said PWD, and GPS and DGPS which may be stored by the PWD.

9. A method as set forth in claim 8 and further comprising determining when said tranceiving unit has traveled a predetermined distance and upon said determination of having traveled said predetermined distance, initiating a telephonic contact to a node on said telephone network.

10. A method as set forth in claim 8 and further comprising:

awaiting a determination of an emergency condition having occurred, then initiating a telephonic contact to at least one node on said telephone network when as emergency condition has arisen.

11. A method as set forth in claim 10 and further comprising:

sending coded data regarding-the nature of the emergency to said at least one node.

12. A method as set forth in claim 10 and further comprising:

sending location data regarding the location of the PWD to said at least one node.

13. A method as set forth in claim 8 and further comprising:

awaiting a determination of an emergency condition having occurred, then initiating a telephonic contact to an emergency system including a system of the two systems, standard emergency system and/or to an E-911 system, on said telephone network when as emergency condition has arisen.

14. A method as set forth in claim 3 and further comprising:

sending coded data regarding nature of the emergency to said emergency system.

15. A method as set forth in claim 13 and further comprising:

sending location data regarding the location of the PWD to said emergency system.

16. A method as set forth in claim 8 and further comprising providing a real time clock system and a clock updating system for correcting the value of real time clock information based on satellite signals to said transceiver unit, automatically using the corrected real time clock values to trigger an automatic turn on a communication between said PWD and a node in a narrow time slice, and reporting to said node by said PWD some or all data facilitated for transfer on that communications pathway.

17. A method as set forth in claim 16 further comprising, receiving command data from said node by said PWD during an additional narrow time slice.

18. A method as set forth in claim 17 further comprising, transmitting a representation of said command data to said IMD from said PWD.

19. A method as set forth in claim 18 further comprising;

receiving said representation of said command data in said IMD, programming the IMD based on said representation of said command data.

[20. A method of monitoring a patient having a transceiver associated therewith and an implanted medical device in communication with said transceiver comprising;

monitoring GPS and DGPS location data by said transceiver, interpreting said location data by said transceiver and if said location data interpreted by said transceiver indicates the patient transceiver is outside a predetermined area, initiating a telephone call by said transceiver to a telephone node on a telephone network, indicating the present location of said transceiver.]

21. A method of monitoring a patient having a transceiver associated therewith and an implanted medical device in communication with said transceiver comprising;

*receiving a command via a medical support network communicatively coupled to said transceiver;*

*monitoring said implanted medical device in accordance with said command, including* monitoring the implanted medical device for *an alarm condition associated with* either a lack of signal over a predetermined period of time or [for] an alarm signal generated by said implanted medical device*;* and if either said alarm signal is received or if said lack of signal exists over said predetermined period of time, automatically initiating an emergency telephone call by said transceiver to a node on a telephone network indicating [an] *said* alarm condition to said node.

22. A method of operating an emergency patient location system comprising, providing said system with patients having implanted medical devices and transceiver units for monitoring communications from said implanted medical devices, providing said transceiver units with means to receive GPS data and to store said GPS data, providing said transceiver units with telecommunications equipment, awaiting the development of emergency conditions to be reported by said transceiver units to said system across telephonic communications pathways, dispatching emergency mobile units having receiver means tuned to receive signals from said transceiver unit reporting said emergency condition, reporting from said transceiver unit location information, receiving said location information in said emergency mobile unit and employing said location information by said emergency mobile unit to locate the patient having the reported emergency.

23. Method as set forth in claim 22 further comprising continuously transmitting a signal by said transceiver unit after reporting said emergency condition and wherein said employing step includes triangulation on a signal transmitted by said transceiver unit after said transceiver unit initially reports said emergency condition.

24. Method as set forth in claim 22 wherein said location information transmitted by said transceiver unit includes DGPS information.

25. Method as set forth in claim 22 wherein said location information transmitted by said transceiver unit includes dead reckoning information.

26. A system for communicating with a medical clinic implanted in an ambulatory patient and for locating the patient to selectively monitor the functions of the medical clinic and provide assistance to and communications with the patient, the system comprising:

an implanted device telemetry transceiver within the implanted medical clinic for communicating data and operating instructions to and from the medical device, the implanted medical device telemetry transceiver having a transceiving range extending outside the patient's body, a distance sufficient to receive and transmit such telemetered communication;

a communications network interface means coupled to a system controller and a communications means for selectively enabling to transmit positioning data to a medical support network and for selectively receiving commands from the medical support network wherein an implantable wireless interface including a real time clock and a system for updating said real time clock based on accurate time clock information in signals received from a global positioning system is integrated therewith;

dead reckoning circuit means for determining the relative location of said transceiver over time to any location at a fixed time during which an acceptable fixed location of said transceiver is known, and wherein a circuit means for producing a representation of received location information for presentation to a telecommunications module is configured to also provide a representation of said dead reckoning information to said telecommunications module; and a distance traveled interpretive processor for receiving an output from said dead reckoning circuit and determining a distance traveled therefrom;

a trigger circuit for triggering the initiation of transmission to a telephone system by said telecommunications module including said communications means when the distance traveled interpretive processor determines a distance traveled is greater than a predetermined trigger distance value.

*27. The method of claim 21, further including programming said implanted medical device in accordance with said command.*

*28. The method of claim 27, wherein programming said implanted medical device includes altering an operating mode of said implanted medical device.*

*29. The method of claim 28, wherein altering an operating mode includes altering a pacing mode of said implanted medical device.*

*30. The method of claim 27, wherein programming said implanted medical device includes altering a parameter of said implanted medical device.*

*31. The method of claim 21, wherein said command is an encoded command.*

*32. The method of claim 21, further including:*

*generating, via said implanted medical device, patient data; and*

*transmitting said patient data to said medical support network in accordance with said command.*

*33. The method of claim 32, wherein transmitting said patient data is performed periodically in accordance with said command.*

*34. The method of claim 21, further including configuring said transceiver in accordance with said command, wherein said command specifies whether said transceiver is to initiate said emergency telephone call in response to said alarm condition.*

*35. The method of claim 21, further including specifying said predetermined period of time within said command.*

*36. The method of claim 21, further including specifying said alarm signal within said command.*

*37. The method of claim 21, wherein monitoring said implanted medical device further comprises the step of displaying information to the patient.*

*38. The method of claim 37, wherein monitoring said implanted medical device further comprises receiving information from the patient via a patient activator.*

*39. The method of claim 21, wherein monitoring said implanted medical device further comprises monitoring said implanted medical device via a monitor worn by the patient.*

*40. The method of claim 39, wherein monitoring said implanted medical device further comprises monitoring said implanted medical device via the monitor worn by the patient in one of a wrist-worn, belt worn or pocket carried monitor device.*

*41. The method of claim 21, wherein monitoring said implanted medical device further comprises monitoring said implanted medical device via a monitor positioned within communication range of the implanted medical device.*

*42. The method of claim 41, wherein monitoring said implanted medical device further comprises monitoring said implanted medical device via the monitor positioned within communication range of the implanted medical device near where the patient sleeps.*

*43. The method of claim 21, further comprising transmitting patient data to a medical network.*

*44. The method of claim 21, further comprising transmitting stored ECG histograms of patient data to a medical network.*

*45. The method of claim 44, further comprising transmitting marker channel information to the medical network.*

*46. The method of claim 21, further comprising transmitting real-time ECG data of the patient to a medical network.*

*47. The method of claim 21, further comprising transmitting measured physical parameters of the patient to a medical network.*

*48. The method of claim 21, wherein automatically initiating an emergency telephone call by said transceiver comprises initiating the emergency telephone call over a hardwired phone line coupled to a telephone network.*

*49. The method of claim 21, wherein automatically initiating an emergency telephone call by said transceiver comprises the step of initiating the emergency telephone call over a cellular telephone network.*

*50. The method of claim 21, wherein automatically initiating an emergency telephone call by said transceiver comprises the step of initiating the emergency telephone call over a cordless telephone network.*

*51. The method of claim 21, further comprising sending an email message to a medical network.*

*52. The method of claim 21, further comprising recharging a battery within a monitoring device that monitors the implanted medical device.*

*53. The method of claim 21, further comprising monitoring the implanted medical device responsive to a command initiated by a patient.*

*54. The method of claim 21, wherein the command causes at least one of a clock or timer to be at least one of adjusted or reprogrammed.*

*55. A method of monitoring a patient having a transceiver associated therewith and an implanted medical device in communication with the transceiver comprising:*

*receiving a command via a medical support network communicatively coupled to the transceiver;*

*monitoring the implanted medical device in accordance with the command, including monitoring the implanted medical device for an alarm condition associated with either a lack of signal over a predetermined period of time or an alarm signal generated by the implanted medical device; and*

*if either the alarm signal is received or if the lack of signal exists over the predetermined period of time,*

*automatically initiating an emergency telephone call by the transceiver to a node on a telephone network indicating the alarm condition to the node and transmitting patient data to a medical network.*

*56. The method of claim 55, wherein transmitting patient data to the medical network includes transmitting stored ECG histograms of patient data to the medical network.*

*57. The method of claim 55, wherein transmitting patient data to the medical network includes transmitting marker channel information to the medical network.*

*58. The method of claim 55, wherein transmitting patient data to the medical network includes transmitting real-time ECG data of the patient to the medical network.*

*59. The method of claim 55, wherein transmitting patient data to the medical network includes transmitting measured physical parameters of the patient to the medical network.*

*60. The method of claim 55, wherein automatically initiating the emergency telephone call by the transceiver comprises initiating the emergency telephone call over a hardwired phone line coupled to the telephone network.*

*61. The method of claim 55, wherein automatically initiating the emergency telephone call by the transceiver comprises initiating the emergency telephone call over a cellular telephone network.*

*62. The method of claim 55, wherein transmitting the patient data is performed periodically in accordance with the command.*

*63. A method of monitoring a patient having a transceiver associated therewith and an implanted medical device in communication with the transceiver comprising:*

*receiving a command via a medical support network communicatively coupled to the transceiver;*

*monitoring said implanted medical device in accordance with the command or responsive to a patient activated command, including monitoring the implanted medical*

*device for an alarm condition associated with either a lack of signal over a predetermined period of time or an alarm signal generated by the implanted medical device; and*

*if either the alarm signal is received or if said lack of signal exists over the predetermined period of time,*

*automatically initiating an emergency telephone call by said transceiver to a node on a telephone network indicating the alarm condition to said node and transmitting patient data to a medical network.*

*64. The method of claim 63, wherein transmitting patient data to the medical network includes transmitting stored ECG histograms of patient data to the medical network.*

*65. The method of claim 63, wherein transmitting patient data to the medical network includes transmitting marker channel information to the medical network.*

*66. The method of claim 63, wherein transmitting patient data to the medical network includes transmitting real-time ECG data of the patient to the medical network.*

*67. The method of claim 63, wherein transmitting patient data to the medical network includes transmitting measured physical parameters of the patient to the medical network.*

*68. The method of claim 63, wherein automatically initiating the emergency telephone call by the transceiver comprises initiating the emergency telephone call over a hard-wired phone line in coupled to the telephone network.*

*69. The method of claim 63, wherein automatically initiating the emergency telephone call by the transceiver comprises initiating the emergency telephone call over a cellular telephone network.*

*70. The method of claim 63, wherein transmitting the patient data is performed periodically in accordance with the command.*

* * * * *